United States Patent
Gori et al.

(10) Patent No.: US 11,634,665 B2
(45) Date of Patent: *Apr. 25, 2023

(54) DETERGENT COMPOSITION

(71) Applicant: NOVOZYMES A/S, Bagsvaerd (DK)

(72) Inventors: Klaus Gori, Dyssegaard (DK); Rune Lyngklip Jensen, Bagsvaerd (DK); Henrik Lund, København N (DK)

(73) Assignee: NOVOZYMES A/S, Bagsvaerd (DK)

( * ) Notice: Subject to any disclaimer, the term of this patent is extended or adjusted under 35 U.S.C. 154(b) by 3 days.

This patent is subject to a terminal disclaimer.

(21) Appl. No.: 17/159,213

(22) Filed: Jan. 27, 2021

(65) Prior Publication Data

US 2021/0163853 A1 Jun. 3, 2021

Related U.S. Application Data

(63) Continuation of application No. 15/562,180, filed as application No. PCT/EP2016/057912 on Apr. 11, 2016, now abandoned.

(30) Foreign Application Priority Data

Apr. 10, 2015 (EP) .................................... 15163230

(51) Int. Cl.
    *C12N 9/22* (2006.01)
    *C11D 3/386* (2006.01)
    *C11D 1/22* (2006.01)
    *C11D 1/29* (2006.01)
    *C11D 11/00* (2006.01)
    *C11D 1/72* (2006.01)
    *C11D 17/00* (2006.01)

(52) U.S. Cl.
CPC ............ *C11D 3/38636* (2013.01); *C11D 1/22* (2013.01); *C11D 1/29* (2013.01); *C11D 1/72* (2013.01); *C11D 11/0017* (2013.01); *C11D 17/0017* (2013.01); *C12N 9/22* (2013.01); *C12Y 301/21001* (2013.01)

(58) Field of Classification Search
None
See application file for complete search history.

(56) References Cited

U.S. PATENT DOCUMENTS 6,242,405 B1    6/2001   Lykke
2017/0107457 A1   4/2017   Gori

FOREIGN PATENT DOCUMENTS

WO   2011/098579 A1   8/2011
WO   2014/087011 A1   6/2014

OTHER PUBLICATIONS

Ngo et al. in the Protein Folding Problem and Tertiary Structure Prediction, 1994, Merz et al. (ed.), Birkhauser, Boston, MA, pp. 433 and 492-495.*
Kravetz et al., Journal of the American Oil Chemists' Society, vol. 62, No. 5, pp. 943-949 (1985).
Otzen, Biochimica et Biophysica Acta, vol. 1814, pp. 562-591 (2011).
Whitchurch et al., Science, vol. 295, p. 1487 (2002).

* cited by examiner

*Primary Examiner* — Richard G Hutson
(74) *Attorney, Agent, or Firm* — Elias Lambiris

(57) ABSTRACT

The present invention concerns a detergent comprising a deoxyribonuclease (DNase). The present invention further relates to methods and uses of the detergent comprising a deoxyribonuclease (DNase) for laundering.

17 Claims, No Drawings
Specification includes a Sequence Listing.

SEQUENCE LISTING

```
<160> NUMBER OF SEQ ID NOS: 7

<210> SEQ ID NO 1
<211> LENGTH: 243
<212> TYPE: PRT
<213> ORGANISM: Aspergillus oryzae
<220> FEATURE:
<221> NAME/KEY: SIGNAL
<222> LOCATION: (1)..(22)
<220> FEATURE:
<221> NAME/KEY: PROPEP
<222> LOCATION: (23)..(37)
<220> FEATURE:
<221> NAME/KEY: CHAIN
<222> LOCATION: (38)..(243)
<223> OTHER INFORMATION: mature polypeptide

<400> SEQUENCE: 1

Met Gln Leu Thr Lys Ser Leu Leu Val Phe Ala Leu Tyr Met Phe Gly
1               5                  10                  15

Thr Gln His Val Leu Ala Val Pro Val Asn Pro Glu Pro Asp Ala Thr
            20                  25                  30

Ser Val Glu Asn Val Ala Leu Lys Thr Gly Ser Gly Asp Ser Gln Ser
        35                  40                  45

Asp Pro Ile Lys Ala Asp Leu Glu Val Lys Gly Gln Ser Ala Leu Pro
    50                  55                  60

Phe Asp Val Asp Cys Trp Ala Ile Leu Cys Lys Gly Ala Pro Asn Val
65                  70                  75                  80

Leu Gln Arg Val Asn Glu Lys Thr Lys Asn Ser Asn Arg Asp Arg Ser
                85                  90                  95
```

Gly Ala Asn Lys Gly Pro Phe Lys Asp Pro Gln Lys Trp Gly Ile Lys
                100                 105                 110

Ala Leu Pro Pro Lys Asn Pro Ser Trp Ser Ala Gln Asp Phe Lys Ser
            115                 120                 125

Pro Glu Glu Tyr Ala Phe Ala Ser Ser Leu Gln Gly Gly Thr Asn Ala
        130                 135                 140

Ile Leu Ala Pro Val Asn Leu Ala Ser Gln Asn Ser Gln Gly Gly Val
145                 150                 155                 160

Leu Asn Gly Phe Tyr Ser Ala Asn Lys Val Ala Gln Phe Asp Pro Ser
                165                 170                 175

Lys Pro Gln Gln Thr Lys Gly Thr Trp Phe Gln Ile Thr Lys Phe Thr
            180                 185                 190

Gly Ala Ala Gly Pro Tyr Cys Lys Ala Leu Gly Ser Asn Asp Lys Ser
        195                 200                 205

Val Cys Asp Lys Asn Lys Asn Ile Ala Gly Asp Trp Gly Phe Asp Pro
210                 215                 220

Ala Lys Trp Ala Tyr Gln Tyr Asp Glu Lys Asn Asn Lys Phe Asn Tyr
225                 230                 235                 240

Val Gly Lys

<210> SEQ ID NO 2
<211> LENGTH: 206
<212> TYPE: PRT
<213> ORGANISM: Aspergillus oryzae
<220> FEATURE:
<221> NAME/KEY: CHAIN
<222> LOCATION: (1)..(206)
<223> OTHER INFORMATION: mature polypeptide

<400> SEQUENCE: 2

Ala Leu Lys Thr Gly Ser Gly Asp Ser Gln Ser Asp Pro Ile Lys Ala
1               5                   10                  15

Asp Leu Glu Val Lys Gly Gln Ser Ala Leu Pro Phe Asp Val Asp Cys
            20                  25                  30

Trp Ala Ile Leu Cys Lys Gly Ala Pro Asn Val Leu Gln Arg Val Asn
        35                  40                  45

Glu Lys Thr Lys Asn Ser Asn Arg Asp Arg Ser Gly Ala Asn Lys Gly
    50                  55                  60

Pro Phe Lys Asp Pro Gln Lys Trp Gly Ile Lys Ala Leu Pro Pro Lys
65                  70                  75                  80

Asn Pro Ser Trp Ser Ala Gln Asp Phe Lys Ser Pro Glu Glu Tyr Ala
                85                  90                  95

Phe Ala Ser Ser Leu Gln Gly Gly Thr Asn Ala Ile Leu Ala Pro Val
            100                 105                 110

Asn Leu Ala Ser Gln Asn Ser Gln Gly Gly Val Leu Asn Gly Phe Tyr
        115                 120                 125

Ser Ala Asn Lys Val Ala Gln Phe Asp Pro Ser Lys Pro Gln Gln Thr
    130                 135                 140

Lys Gly Thr Trp Phe Gln Ile Thr Lys Phe Thr Gly Ala Ala Gly Pro
145                 150                 155                 160

Tyr Cys Lys Ala Leu Gly Ser Asn Asp Lys Ser Val Cys Asp Lys Asn
                165                 170                 175

Lys Asn Ile Ala Gly Asp Trp Gly Phe Asp Pro Ala Lys Trp Ala Tyr
            180                 185                 190

Gln Tyr Asp Glu Lys Asn Asn Lys Phe Asn Tyr Val Gly Lys
        195                 200                 205

<210> SEQ ID NO 3
<211> LENGTH: 204
<212> TYPE: PRT
<213> ORGANISM: Aspergillus oryzae
<220> FEATURE:
<221> NAME/KEY: CHAIN
<222> LOCATION: (1)..(204)
<223> OTHER INFORMATION: mature polypeptide

<400> SEQUENCE: 3

Lys Thr Gly Ser Gly Asp Ser Gln Ser Asp Pro Ile Lys Ala Asp Leu
1               5                   10                  15

Glu Val Lys Gly Gln Ser Ala Leu Pro Phe Asp Val Asp Cys Trp Ala
            20                  25                  30

Ile Leu Cys Lys Gly Ala Pro Asn Val Leu Gln Arg Val Asn Glu Lys
        35                  40                  45

Thr Lys Asn Ser Asn Arg Asp Arg Ser Gly Ala Asn Lys Gly Pro Phe
    50                  55                  60

Lys Asp Pro Gln Lys Trp Gly Ile Lys Ala Leu Pro Pro Lys Asn Pro
65                  70                  75                  80

Ser Trp Ser Ala Gln Asp Phe Lys Ser Pro Glu Glu Tyr Ala Phe Ala
                85                  90                  95

Ser Ser Leu Gln Gly Gly Thr Asn Ala Ile Leu Ala Pro Val Asn Leu
            100                 105                 110

Ala Ser Gln Asn Ser Gln Gly Gly Val Leu Asn Gly Phe Tyr Ser Ala
        115                 120                 125

Asn Lys Val Ala Gln Phe Asp Pro Ser Lys Pro Gln Gln Thr Lys Gly
    130                 135                 140

Thr Trp Phe Gln Ile Thr Lys Phe Thr Gly Ala Ala Gly Pro Tyr Cys
145                 150                 155                 160

Lys Ala Leu Gly Ser Asn Asp Lys Ser Val Cys Asp Lys Asn Lys Asn
                165                 170                 175

Ile Ala Gly Asp Trp Gly Phe Asp Pro Ala Lys Trp Ala Tyr Gln Tyr
            180                 185                 190

Asp Glu Lys Asn Asn Lys Phe Asn Tyr Val Gly Lys
        195                 200

<210> SEQ ID NO 4
<211> LENGTH: 205
<212> TYPE: PRT
<213> ORGANISM: Trichoderma harzianum
<220> FEATURE:
<221> NAME/KEY: SIGNAL
<222> LOCATION: (1)..(17)
<220> FEATURE:
<221> NAME/KEY: CHAIN
<222> LOCATION: (18)..(205)
<223> OTHER INFORMATION: mature polypeptide

<400> SEQUENCE: 4

Met Lys Leu Ser Ile Ser Val Ala Leu Thr Ser Ala Ile Ala Val Leu
1               5                   10                  15

Ala Ala Pro Ala Pro Met Pro Thr Pro Pro Gly Ile Pro Thr Glu Ser
            20                  25                  30

Ser Ala Arg Thr Gln Leu Ala Gly Leu Thr Val Ala Val Ala Gly Ser
        35                  40                  45

Gly Thr Gly Tyr Ser Arg Asp Leu Phe Pro Thr Trp Asp Ala Ile Ser
    50                  55                  60

```
Gly Asn Cys Asn Ala Arg Glu Tyr Val Leu Lys Arg Asp Gly Glu Gly
 65                  70                  75                  80

Val Gln Val Asn Ala Cys Glu Ser Gln Ser Gly Thr Trp Ile Ser
                 85                  90                  95

Pro Tyr Asp Asn Ala Ser Phe Thr Asn Ala Ser Ser Leu Asp Ile Asp
                100                 105                 110

His Met Val Pro Leu Lys Asn Ala Trp Ile Ser Gly Ala Ser Ser Trp
                115                 120                 125

Thr Thr Ala Gln Arg Glu Ala Leu Ala Asn Asp Val Ser Arg Pro Gln
130                 135                 140

Leu Trp Ala Val Ser Ala Ser Ala Asn Arg Ser Lys Gly Asp Arg Ser
145                 150                 155                 160

Pro Asp Gln Trp Lys Pro Pro Leu Thr Ser Phe Tyr Cys Thr Tyr Ala
                165                 170                 175

Lys Ser Trp Ile Asp Val Lys Ser Phe Tyr Lys Leu Thr Ile Thr Ser
                180                 185                 190

Ala Glu Lys Thr Ala Leu Ser Ser Met Leu Asp Thr Cys
                195                 200                 205

<210> SEQ ID NO 5
<211> LENGTH: 142
<212> TYPE: PRT
<213> ORGANISM: Bacillus licheniformis
<220> FEATURE:
<221> NAME/KEY: SIGNAL
<222> LOCATION: (1)..(33)
<220> FEATURE:
<221> NAME/KEY: CHAIN
<222> LOCATION: (34)..(142)
<223> OTHER INFORMATION: mature polypeptide

<400> SEQUENCE: 5

Met Ile Lys Lys Trp Ala Val His Leu Leu Phe Ser Ala Leu Val Leu
1               5                   10                  15

Leu Gly Leu Ser Gly Gly Ala Ala Tyr Ser Pro Gln His Ala Glu Gly
                20                  25                  30

Ala Ala Arg Tyr Asp Asp Ile Leu Tyr Phe Pro Ala Ser Arg Tyr Pro
                35                  40                  45

Glu Thr Gly Ala His Ile Ser Asp Ala Ile Lys Ala Gly His Ser Asp
 50                  55                  60

Val Cys Thr Ile Glu Arg Ser Gly Ala Asp Lys Arg Gln Glu Ser
 65                  70                  75                  80

Leu Lys Gly Ile Pro Thr Lys Pro Gly Phe Asp Arg Asp Glu Trp Pro
                85                  90                  95

Met Ala Met Cys Glu Glu Gly Gly Lys Gly Ala Ser Val Arg Tyr Val
                100                 105                 110

Ser Ser Ser Asp Asn Arg Gly Ala Gly Ser Trp Val Gly Asn Arg Leu
                115                 120                 125

Ser Gly Phe Ala Asp Gly Thr Arg Ile Leu Phe Ile Val Gln
130                 135                 140

<210> SEQ ID NO 6
<211> LENGTH: 136
<212> TYPE: PRT
<213> ORGANISM: Bacillus subtilis
<220> FEATURE:
<221> NAME/KEY: SIGNAL
<222> LOCATION: (1)..(26)
<220> FEATURE:
<221> NAME/KEY: CHAIN
```

<222> LOCATION: (27)..(136)
<223> OTHER INFORMATION: mature polypeptide

<400> SEQUENCE: 6

```
Met Lys Lys Trp Met Ala Gly Leu Phe Leu Ala Ala Val Leu Leu
1               5                   10                  15

Cys Leu Met Val Pro Gln Gln Ile Gln Gly Ala Ser Ser Tyr Asp Lys
            20                  25                  30

Val Leu Tyr Phe Pro Leu Ser Arg Tyr Pro Glu Thr Gly Ser His Ile
                35                  40                  45

Arg Asp Ala Ile Ala Glu Gly His Pro Asp Ile Cys Thr Ile Asp Arg
        50                  55                  60

Asp Gly Ala Asp Lys Arg Arg Glu Glu Ser Leu Lys Gly Ile Pro Thr
65                  70                  75                  80

Lys Pro Gly Tyr Asp Arg Asp Glu Trp Pro Met Ala Val Cys Glu Glu
                85                  90                  95

Gly Gly Ala Gly Ala Asp Val Arg Tyr Val Thr Pro Ser Asp Asn Arg
            100                 105                 110

Gly Ala Gly Ser Trp Val Gly Asn Gln Met Ser Ser Tyr Pro Asp Gly
        115                 120                 125

Thr Arg Val Leu Phe Ile Val Gln
    130                 135
```

<210> SEQ ID NO 7
<211> LENGTH: 269
<212> TYPE: PRT
<213> ORGANISM: Bacillus lentus

<400> SEQUENCE: 7

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205
```

-continued

```
Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

DETERGENT COMPOSITION

CROSS-REFERENCE TO RELATED APPLICATIONS

This application is a continuation of U.S. application Ser. No. 15/562,180 filed Sep. 27, 2017, now abandoned, which is a 35 U.S.C. 371 national application of international application no. PCT/EP2016/057912 filed Apr. 11, 2016, which claims priority or the benefit under 35 U.S.C. 119 of European application no. 15163230.4 filed Apr. 10, 2015. The content of each application is fully incorporated herein by reference.

REFERENCE TO A SEQUENCE LISTING

This application contains a Sequence Listing in computer readable form. The computer readable form is incorporated herein by reference.

FIELD OF THE INVENTION

The present invention concerns a detergent comprising a deoxyribonuclease (DNase). The present invention further relates to methods and uses of the detergent comprising a deoxyribonuclease (DNase) for laundering.

BACKGROUND OF THE INVENTION

Microorganisms generally live attached to surfaces in many natural, industrial, and medical environments, encapsulated by extracellular substances including biopolymers and macromolecules. The resulting layer of slime encapsulated microorganism is termed a biofilm. Biofilms are the predominant mode of growth of bacteria in the natural environment, and bacteria growing in biofilms exhibit distinct physiological properties. Compared to their planktonically grown counterparts, the bacteria in a biofilm are more resistant to antibiotics, UV irradiation, detergents and the host immune response.

It has for many years been a known problem that laundry items like shirts and blouses become more and more grey as time goes by. For normal day clothing as well as sportswear sweat and the resulting odor is a challenge. These stains usually consist of a lot of different components adhering to the textile of the clothing and can be difficult to dissolve and remove. When laundry items like T-shirts or sportswear are used, they are contacted to sweat and bacteria from the body of the user and for other kinds of dirt from the rest of the environment in which they are used. Some of these bacteria are capable of adhering to the laundry item and form a biofilm on the item. The presence of bacteria implies that the laundry items become sticky and therefore soil adheres to the sticky areas. This soil has shown difficult to remove by commercially available detergent compositions. Further, when very dirty laundry items are washed together with less dirty laundry items the dirt present in the wash liquor tend to stick to the biofilm. As a result hereof the laundry item is more "soiled" and more grey after wash than before wash.

Sportswear is a good example, because there is often soil, clay and traffic dirt on the clothes washed together with very sweaty shirts. From wash to wash the clothes become more and more grey and they eventually appear as developed spots. This kind of dirt is one reason why people discard their clothes. Although the problem is well known to most garment the problem is very pronounced for mixed fabrics. There is a European political desire to conserve resources for laundry which has led to their adoption of a labeling law for washing machines in the EU to exclude machines with high demand. This means that cold water washing is much more prevalent in the EU and thus has come to resemble the rest of the world wash circumstances better. However, the saving of energy by washing at lower temperature may lead to consumers discarding clothes and buying new because the sweat stains are not properly removed.

WO 2011/098579 concerns bacterial deoxyribonuclease compounds and methods for biofilm disruption and prevention. WO 2014/087011 concerns detergent compositions comprising one or more anionic surfactants, a bacterial deoxyribonuclease and a further enzyme selected from the group consisting of a protease, a lipase, a cutinase, an amylase, a carbohydrase, a cellulase, a pectinase, a mannanase, an arabinase, a galactanase, a xylanase, and an oxidase.

SUMMARY OF THE INVENTION

In a first aspect, the invention provides a detergent composition comprising:
   (i) a polypeptide having deoxyribonuclease activity,
   (ii) at least one surfactant,
wherein the total amount of surfactant(s) in said composition is in the range of 3.6 w/w % to 28.5 w/w %.

A second aspect concerns a method for preventing, reducing or removing biofilm from a textile or fabric comprising:
   (i) contacting the a textile or fabric at least partly coated with a biofilm with a wash liquor comprising the detergent composition of the present invention,
   (ii) subjecting said textile to at least one washing cycle,
   (iii) optionally rinsing said textile.

A third aspect concerns the use of the detergent composition of the present invention for preventing, reducing or removing biofilm from a textile or a fabric.

Definitions

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Biofilm: A biofilm is any group of microorganisms in which cells stick to each other on a surface, such as a textile, dishware or hard surface. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces. The microbial cells growing in a biofilm are physiologically distinct from planktonic cells of the same organism, which, by contrast, are single-cells that may float or swim in a liquid medium.

Bacteria living in a biofilm usually have significantly different properties from free-floating bacteria of the same species, as the dense and protected environment of the film allows them to cooperate and interact in various ways. One benefit of this environment is increased resistance to detergents and antibiotics, as the dense extracellular matrix and the outer layer of cells protect the interior of the community.

On laundry biofilm producing bacteria can be found among the following species: *Acinetobacter* sp., *Aeromicrobium* sp., *Brevundimonas* sp., *Microbacterium* sp., *Micro-*

*coccus luteus, Pseudomonas* sp., *Staphylococcus epidermidis*, and *Stenotrophomonas* sp.

Color difference (L value): A Lab color space is a color-opponent space with dimension L for lightness. L value, L* represents the darkest black at L*=0, and the brightest white at L*=100. In the context of the present invention L value is also referred to as color difference.

Detergent adjunct ingredient: The detergent adjunct ingredient is different to the DNase of this invention. The precise nature of these additional adjunct components, and levels of incorporation thereof, will depend on the physical form of the composition and the nature of the operation for which it is to be used. Suitable adjunct materials include, but are not limited to the components described below such as surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric huing agents, anti-foaming agents, dispersants, processing aids, and/or pigments.

Detergent Composition: The term "detergent composition" refers to compositions that find use in the removal of undesired compounds from items to be cleaned, such as textiles. The detergent composition may be used to, e.g., clean textiles for both household cleaning and industrial cleaning. The terms encompass any materials/compounds selected for the particular type of cleaning composition desired and the form of the product (e.g., liquid, gel, powder, granulate, paste, or spray compositions) and includes, but is not limited to, detergent compositions (e.g., liquid and/or solid laundry detergents and fine fabric detergents; fabric fresheners; fabric softeners; and textile and laundry pre-spotters/pretreatment). In addition to containing the enzyme of the invention, the detergent formulation may contain one or more additional enzymes (such as proteases, amylases, lipases, cutinases, cellulases, endoglucanases, xyloglucanases, pectinases, pectin lyases, xanthanases, peroxidases, haloperoxygenases, catalases and mannanases, or any mixture thereof), and/or detergent adjunct ingredients such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

DNase (deoxyribonuclease): The term "DNase" means a polypeptide with DNase activity that catalyzes the hydrolytic cleavage of phosphodiester linkages in the DNA backbone, thus degrading DNA. For purposes of the present invention, DNase activity is determined according to the procedure described in the Assay I. In one embodiment of the present invention, the DNase activity of polypeptide having is at least 105%, e.g., at least 110%, at least 120%, at least 130%, at least 140%, at least 160%, at least 170%, at least 180%, or at least 200% with reference to the DNase activity of the mature polypeptide of SEQ ID NO: 1, a polypeptide comprising or consisting of the sequence set forth in SEQ ID NO: 2, a polypeptide comprising or consisting of the sequence set forth in SEQ ID NO: 3, a polypeptide comprising or consisting of the mature polypeptide of SEQ ID NO: 4, a polypeptide comprising or consisting of the mature polypeptide of SEQ ID NO: 5 or a polypeptide comprising or consisting of the mature polypeptide of SEQ ID NO: 6.

Enzyme Detergency benefit: The term "enzyme detergency benefit" is defined herein as the advantageous effect an enzyme may add to a detergent compared to the same detergent without the enzyme. Important detergency benefits which can be provided by enzymes are stain removal with no or very little visible soils after washing and/or cleaning, prevention or reduction of redeposition of soils released in the washing process (an effect that also is termed anti-redeposition), restoring fully or partly the whiteness of textiles which originally were white but after repeated use and wash have obtained a greyish or yellowish appearance (an effect that also is termed whitening). Textile care benefits, which are not directly related to catalytic stain removal or prevention of redeposition of soils, are also important for enzyme detergency benefits. Examples of such textile care benefits are prevention or reduction of dye transfer from one fabric to another fabric or another part of the same fabric (an effect that is also termed dye transfer inhibition or anti-backstaining), removal of protruding or broken fibers from a fabric surface to decrease pilling tendencies or remove already existing pills or fuzz (an effect that also is termed anti-pilling), improvement of the fabric-softness, colour clarification of the fabric and removal of particulate soils which are trapped in the fibers of the fabric or garment. Enzymatic bleaching is a further enzyme detergency benefit where the catalytic activity generally is used to catalyze the formation of bleaching components such as hydrogen peroxide or other peroxides.

Fragment: The term "fragment" means a polypeptide having one or more (e.g., several) amino acids absent from the amino and/or carboxyl terminus of a mature polypeptide or domain; wherein the fragment has DNase activity. In one embodiment, a fragment contains at least 206 amino acid residues (e.g., amino acids 38 to 243 of SEQ ID NO: 1), at least 205 amino acid residues (e.g., amino acids 39 to 243 of SEQ ID NO: 1), or at least 204 amino acid residues (e.g., amino acids 40 to 243 of SEQ ID NO: 1).

Bacterial: In the context of the present invention, the term "bacterial" in relation to polypeptide (such as an enzyme, e.g., a DNase) refers to a polypeptide encoded by and thus directly derivable from the genome of a bacteria, where such bacteria has not been genetically modified to encode said polypeptide, e.g., by introducing the encoding sequence in the genome by recombinant DNA technology. In the context of the present invention, the term "bacterial DNase" or "polypeptide having DNase activity obtained from a "bacterial source" thus refers to a DNase encoded by and thus directly derivable from the genome of a bacterial species, where the bacterial species has not been subjected to a genetic modification introducing recombinant DNA encoding said DNase. Thus, the nucleotide sequence encoding the bacterial polypeptide having DNase activity is a sequence naturally in the genetic background of a bacterial species. The bacterial polypeptide having DNase activity encoding by such sequence may also be referred to a bacterial wild-type DNase (or bacterial parent DNase). In a further embodiment, the polypeptides having DNase activity are substantially homologous to a bacterial DNase. In the context of the present invention, the term "substantially homologous" denotes a polypeptide having DNase activity which is at least 80%, preferably at least 85%, more preferably at least 90%, more preferably at least 95%, even more preferably at least 96%, 97%, 98%, and most preferably at least 99% identical to the amino acid sequence of a selected bacterial DNase.

Fungal: In the context of the present invention, the term "fungal" in relation to polypeptide (such as an enzyme, e.g., a DNase) refers to a polypeptide encoded by and thus directly derivable from the genome of a fungus, where such fungus has not been genetically modified to encode said polypeptide, e.g., by introducing the encoding sequence in the genome by recombinant DNA technology. In the context of the present invention, the term "fungal DNase" or "polypeptide having DNase activity obtained from a fungal source" thus refers to a DNase encoded by and thus directly derivable from the genome of a fungal species, where the fungal species has not been subjected to a genetic modification introducing recombinant DNA encoding said DNase. Thus, the nucleotide sequence encoding the fungal polypeptide having DNase activity is a sequence naturally in the genetic background of a fungal species. The fungal polypeptide having DNase activity encoding by such sequence may also be referred to a fungal wildtype DNase (or fungal parent DNase). In a further embodiment, the polypeptides having DNase activity are substantially homologous to another DNase. In the context of the present invention, the term "substantially homologous" denotes a polypeptide having DNase activity which is at least 80%, preferably at least 85%, more preferably at least 90%, more preferably at least 95%, even more preferably at least 96%, 97%, 98%, and most preferably at least 99% identical to the amino acid sequence of any of the mature polypeptides of SEQ ID NO: 1, 4, 5 or 6.

Improved wash performance: The term "improved wash performance" is defined herein as an enzyme displaying an increased wash performance in a detergent composition relative to the wash performance of same detergent composition without the enzyme, e.g., by increased stain removal or less redeposition. The term "improved wash performance" includes wash performance in laundry.

Laundering: The term "laundering" relates to both household laundering and industrial laundering and means the process of treating textiles with a solution containing a cleaning or detergent composition of the present invention. The laundering process can for example be carried out using, e.g., a household or an industrial washing machine or can be carried out by hand.

By the term "malodor" is meant an odor which is not desired on clean items. The cleaned item should smell fresh and clean without malodors adhered to the item. One example of malodor is compounds with an unpleasant smell, which may be produced by microorganisms. Another example is unpleasant smells can be sweat or body odor adhered to an item which has been in contact with human or animal. Another example of malodor can be the odor from spices, which sticks to items for example curry or other exotic spices which smells strongly. One way of measuring the ability of an item to adhere malodor is by using Assay II disclosed herein.

Mature polypeptide: The term "mature polypeptide" means a polypeptide in its final form following translation and any post-translational modifications, such as N-terminal processing, C-terminal truncation, glycosylation, phosphorylation, etc. In one embodiment, the mature polypeptide is amino acids 38 to 243 of SEQ ID NO: 1 and amino acids 1 to 22 of SEQ ID NO: 1 are a signal peptide and amino acids 23 to 37 of SEQ ID NO: 1 are a propeptide. It is known in the art that a host cell may produce a mixture of two of more different mature polypeptides with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide. In one embodiment, a mature polypeptides contains up to 206 (such as 204) consecutive amino acid residues of the sequence set forth in SEQ ID NO: 1 or SEQ ID NO: 2 (e.g., amino acids 38 to 243 of SEQ ID NO: 1 or amino acids 1 to 206 of SEQ ID NO: 2 or amino acids 1 to 204 of SEQ ID NO: 3), or up to 204 amino acid residues (e.g., amino acids 40 to 243 of SEQ ID NO: 1). In another embodiment, the mature polypeptide consists of the of the amino acid sequence set forth in SEQ ID NO: 2 or SEQ ID NO: 3. In yet another embodiment, the mature polypeptide comprises or consists of the consecutive amino acid residues 18 to 205 of SEQ ID NO: 4. In one embodiment, the mature polypeptide comprises or consists of the consecutive amino acid residues 34 to 142 of SEQ ID NO: 5. In one embodiment, the mature polypeptide comprises or consists of the consecutive amino acid residues 27 to 136 of SEQ ID NO: 6.

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the-nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the-nobrief option) is used as the percent identity and is calculated as follows:

(Identical Deoxyribonucleotides×100)/(Length of Alignment−Total Number of Gaps in Alignment).

Textile: The term "textile" means any textile material including yarns, yarn intermediates, fibers, non-woven materials, natural materials, synthetic materials, and any other textile material, fabrics made of these materials and products made from fabrics (e.g., garments and other articles). The textile or fabric may be in the form of knits, wovens, denims, non-wovens, felts, yarns, and toweling. The textile may be cellulose based such as natural cellulosics, including cotton, flax/linen, jute, ramie, sisal or coir or manmade cellulosics (e.g., originating from wood pulp)

including viscose/rayon, cellulose acetate fibers (tricell), lyocell or blends thereof. The textile or fabric may also be non-cellulose based such as natural polyamides including wool, camel, cashmere, mohair, rabbit and silk or synthetic polymers such as nylon, aramid, polyester, acrylic, polypropylene and spandex/elastane, or blends thereof as well as blends of cellulose based and non-cellulose based fibers. Examples of blends are blends of cotton and/or rayon/viscose with one or more companion material such as wool, synthetic fiber (e.g., polyamide fiber, acrylic fiber, polyester fiber, polyvinyl chloride fiber, polyurethane fiber, polyurea fiber, aramid fiber), and/or cellulose-containing fiber (e.g., rayon/viscose, ramie, flax/linen, jute, cellulose acetate fiber, lyocell). Fabric may be conventional washable laundry, for example stained household laundry. When the term fabric or garment is used it is intended to include the broader term textiles as well. In the context of the present invention, the term "textile" also covers fabrics.

Variant: The term "variant" means a polypeptide having same activity as the parent enzyme comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. In the context of the present invention, a variant of an identified DNase has the enzymatic activity of the parent, i.e., the capacity of catalyzing the hydrolytic cleavage of phosphodiester linkages in the DNA backbone (deoxyribonuclease activity). In one embodiment, the deoxyribonuclease activity of the variant is increased with reference to the parent DNase, e.g., the mature polypeptide of a polypeptide having deoxyribonuclease activity is selected from the group consisting of a polypeptide comprising or consisting of the mature polypeptide of SEQ ID NO: 1, a polypeptide comprising or consisting of the sequence set forth in SEQ ID NO: 2, a polypeptide comprising or consisting of the sequence set forth in SEQ ID NO: 3, a polypeptide comprising or consisting of the mature polypeptide of SEQ ID NO: 4, a polypeptide comprising or consisting of the mature polypeptide of SEQ ID NO: 5 or a polypeptide comprising or consisting of the mature polypeptide of SEQ ID NO: 6.

Wash cycle: The term "wash cycle" is defined herein as a washing operation wherein textiles are immersed in the wash liquor, mechanical action of some kind is applied to the textile in order to release stains and to facilitate flow of wash liquor in and out of the textile and finally the superfluous wash liquor is removed. After one or more wash cycles, the textile is generally rinsed and dried.

Wash liquor: The term "wash liquor" is defined herein as the solution or mixture of water and detergent components optionally including the enzyme of the invention.

Wash time: The term "wash time" is defined herein as the time it takes for the entire washing process; i.e., the time for the wash cycle(s) and rinse cycle(s) together.

Whiteness: The term "Whiteness" is defined herein as a broad term with different meanings in different regions and for different consumers. Loss of whiteness can, e.g., be due to greying, yellowing, or removal of optical brighteners/hueing agents. Greying and yellowing can be due to soil redeposition, body soils, colouring from, e.g., iron and copper ions or dye transfer. Whiteness might include one or several issues from the list below: colourant or dye effects; incomplete stain removal (e.g., body soils, sebum etc.); redeposition (greying, yellowing or other discolourations of the object) (removed soils reassociate with other parts of textile, soiled or unsoiled); chemical changes in textile during application; and clarification or brightening of colours.

DETAILED DESCRIPTION OF THE INVENTION

Biofilm can develop on textile when microorganisms are present on an item and stick together on the item. Some microorganisms tend to adhere to the surface of items such as textiles. Some microorganisms adhere to such surfaces and form a biofilm on the surface. The biofilm may be sticky and the adhered microorganisms and/or the biofilm may be difficult to remove. Furthermore, the biofilm adhere soil due to the sticky nature of the biofilm. Commercial laundry detergent compositions available on the marked do not remove such adhered microorganisms or biofilm. The inventors have found that polypeptides having deoxyribonuclease (DNase) activity can be used for disrupting/eroding biofilm on textiles and/or fabrics and that the effect of DNase on the disruption/erosion of the biofilm is independent on the amount of surfactant applied. This is surprising as many enzymes are not working optimally if surfactant concentration is lowered from the original concentration. The inventors have found that DNase, however, does not loose performance if surfactant concentration is reduced by, e.g., 30%. Accordingly, detergent composition comprising DNase may be formulated with reduced amount of surfactants without affecting the beneficial effect of the DNase (e.g., when the total amount of surfactant(s) including soap in the detergent composition is in the range of about 3.6 w/w % to about 28.5 w/w %, about 3.0 w/w % to about 35 w/w %, about 5.0 w/w % to about 25 w/w %, about 5.0 w/w % to about 20 w/w %, about 10.0 w/w % to about 20 w/w % or about 10.0 w/w % to about 15 w/w %). The inventors have found that the DNases perform maintain or, e.g., improve its effects on biofilm swatches when the amount of surfactant(s) including soap in the detergents is below 20. This has been shown in example 1, table 2 of the application where the performance of DNases, such as DNase from *A. oryzae* in detergent with different levels of surfactants are compared, e.g., when comparing performance of the DNases, such as *A. oryzae*, in model detergent A with surfactant level (total amount of surfactants including soap) of about 30 (33,5) with the performance of the DNases, *A. oryzae*, in model detergent B with surfactant level (total amount of surfactant with soap) of about 20 (22.1) the performance on biofilm swatches is similar in the two detergents. Thus in some aspects of the invention the detergent composition of the invention comprises: i) a polypeptide having deoxyribonuclease activity and (ii) at least one surfactant, wherein the total amount of surfactant(s) in said detergent composition is reduced by at least 5%, such as at least 10%, such as at least 20% such as at least 30% such as at least 40% such as at least 50% such as at least 60% such as at least 70% such as at least 80% such as at least 90% compared to the original detergent. Reducing the amount of surfactants in detergents is beneficial for the environment and reduces the cost of the detergent compositions.

Detergent Composition of the Invention

A first aspect of the present invention provides a detergent composition comprising:
(i) a polypeptide having deoxyribonuclease activity,
(ii) at least one surfactant,
wherein the total amount of surfactant(s) in said composition is in the range of 3.6 w/w % to 28.5 w/w %, optionally in the range of 3 w/w % to 30 w/w %, optionally in the range of 5 w/w % to 20 w/w %, optionally in the range of 10 w/w % to 20 w/w % or optionally in the range of 15 w/w % to 20 w/w %. If nothing else is mentioned w/w % has its common meaning in the field of laundry detergents and includes the amount of surfactant in the detergent solution, e.g., wherein w/w % means the percent by weight of surfactant in the total weight of detergent solution. If nothing else is mentioned the total amount of surfactant includes soap if one or more soap(s) is present in the detergent. If nothing else is mentioned the term soap has its common meaning in the field of laundry detergents and includes the meaning that soap is a salt of a fatty acid.

In some aspects of the invention the detergent composition of the invention comprises:

i) a polypeptide having DNase activity, such as fungal DNase, and/or such as a DNase having a polypeptide sequence which has at least 60% sequence identity to the mature polypeptide of SEQ ID NO: 1, wherein the activity of the DNase polypeptide is at least 100%, e.g., at least 110%, at least 110%, at least 120%, at least 130%, at least 140%, at least 160%, at least 170%, at least 180%, or at least 200% compared to the to the DNase activity of the mature polypeptide of SEQ ID NO: 1, and ii) at least one surfactant, wherein the total amount of surfactant(s) in the composition is about 25 w/w %, such as about 24 w/w %, such as about 23 w/w %, such as about 22 w/w %, such as about 21 w/w %, such as about 20 w/w %, such as about 19 w/w %, such as about 18 w/w %, such as about 17 w/w %, such as about 16 w/w %, such as about 15 w/w %, such as about 14 w/w %, such as about 13 w/w %, such as about 12 w/w %, such as about 11 w/w %, such as about 10 w/w %, such as about 9 w/w %, such as about 8 w/w %, such as about 7 w/w %, such as about 6 w/w %, such as about 5 w/w %, such as about 4 w/w %, such as about 3 w/w %, such as about 2 w/w %, such as about 1 w/w % or wherein the total amount of surfactant(s) is in the range of about 3.6 w/w % to about 28.5 w/w %, about 3.0 w/w % to about 35 w/w %, about 5.0 w/w % to about 25 w/w %, about 5.0 w/w % to about 20 w/w %, about 10.0 w/w % to about 20 w/w % or about 10.0 w/w % to about 15 w/w %, where total amount of surfactant(s), e.g., one or more surfactant, is the total amount of surfactant(s) (e.g., one or more surfactants) including soap if soap is present in the detergent.

In some aspects of the invention, the detergent composition of the invention comprises:

i) a polypeptide having DNase activity, such as fungal DNase, and/or such as a DNase having a polypeptide sequence which has at least 60% sequence identity to the mature polypeptide of SEQ ID NO: 4, wherein the activity of the DNase polypeptide is at least 100%, e.g., at least 110%, at least 110%, at least 120%, at least 130%, at least 140%, at least 160%, at least 170%, at least 180%, or at least 200% compared to the to the DNase activity of the mature polypeptide of SEQ ID NO: 4, and ii) at least one surfactant, wherein the total amount of surfactant(s) in the composition is about 25 w/w %, such as about 24 w/w %, such as about 23 w/w %, such as about 22 w/w %, such as about 21 w/w %, such as about 20 w/w %, such as about 19 w/w %, such as about 18 w/w %, such as about 17 w/w %, such as about 16 w/w %, such as about 14 w/w %, such as about 13 w/w %, such as about 12 w/w %, such as about 11 w/w %, such as about 10 w/w %, such as about 9 w/w %, such as about 8 w/w %, such as about 7 w/w %, such as about 6 w/w %, such as about 5 w/w %, such as about 4 w/w %, such as about 3 w/w %, such as about 2 w/w %, such as about 1 w/w % or wherein the total amount of surfactant(s) is in the range of about 3.6 w/w % to about 28.5 w/w %, about 3.0 w/w % to about 35 w/w %, about 5.0 w/w % to about 25 w/w %, about 5.0 w/w % to about 20 w/w %, about 10.0 w/w % to about 20 w/w % or about 10.0 w/w % to about 15 w/w %, where total amount of surfactant(s), e.g., one or more surfactant, is the total amount of surfactant(s) (e.g., one or more surfactants) including soap if soap is present in the detergent.

In some aspects of the invention, the detergent composition of the invention comprises: i) a polypeptide having DNase activity, such as *bacillus* DNase, and/or such as a DNase having a polypeptide sequence which has at least 60% sequence identity to the mature polypeptide of SEQ ID NO: 5, wherein the activity of the DNase polypeptide is at least 100%, e.g., at least 110%, at least 110%, at least 120%, at least 130%, at least 140%, at least 160%, at least 170%, at least 180%, or at least 200% compared to the to the DNase activity of the mature polypeptide of SEQ ID NO: 5, and ii) at least one surfactant, wherein the total amount of surfactant(s) in the composition is about 25 w/w %, such as about 24 w/w %, such as about 23 w/w %, such as about 22 w/w %, such as about 21 w/w %, such as about 20 w/w %, such as about 19 w/w %, such as about 18 w/w %, such as about 17 w/w %, such as about 16 w/w %, such as about 15 w/w %, such as about 14 w/w %, such as about 13 w/w %, such as about 12 w/w %, such as about 11 w/w %, such as about 10 w/w %, such as about 9 w/w %, such as about 8 w/w %, such as about 7 w/w %, such as about 6 w/w %, such as about 5 w/w %, such as about 4 w/w %, such as about 3 w/w %, such as about 2 w/w %, such as about 1 w/w % or wherein the total amount of surfactant(s) is in the range of about 3.6 w/w % to about 28.5 w/w %, about 3.0 w/w % to about 35 w/w %, about 5.0 w/w % to about 25 w/w %, about 5.0 w/w % to about 20 w/w %, about 10.0 w/w % to about 20 w/w % or about 10.0 w/w % to about 15 w/w %, where total amount of surfactant(s), e.g., one or more surfactant, is the total amount of surfactant(s) (e.g., one or more surfactants) including soap if soap is present in the detergent.

In some aspects of the invention, the detergent composition of the invention comprises: i) a polypeptide having DNase activity, such as *bacillus* DNase, and/or such as a DNase having a polypeptide sequence which has at least 60% sequence identity to the mature polypeptide of SEQ ID NO: 6, wherein the activity of the DNase polypeptide is at least 100%, e.g., at least 110%, at least 110%, at least 120%, at least 130%, at least 140%, at least 160%, at least 170%, at least 180%, or at least 200% compared to the to the DNase activity of the mature polypeptide of SEQ ID NO: 6, and ii) at least one surfactant, wherein the total amount of surfactant(s) in the composition is about 25 w/w %, such as about 24 w/w %, such as about 23 w/w %, such as about 22 w/w %, such as about 21 w/w %, such as about 20 w/w %, such as about 19 w/w %, such as about 18 w/w %, such as about 17 w/w %, such as about 16 w/w %, such as about 15 w/w %, such as about 14 w/w %, such as about 13 w/w %, such as about 12 w/w %, such as about 11 w/w %, such as about 10 w/w %, such as about 9 w/w %, such as about 8 w/w %, such as about 7 w/w %, such as about 6 w/w %, such as about 5 w/w %, such as about 4 w/w %, such as about 3 w/w %, such as about 2 w/w %, such as about 1 w/w % or wherein the total amount of surfactant(s) is in the range of about 3.6 w/w % to about 28.5 w/w %, about 3.0 w/w % to about 35 w/w %, about 5.0 w/w % to about 25 w/w %, about 5.0 w/w % to about 20 w/w %, about 10.0 w/w % to about 20 w/w % or about 10.0 w/w % to about 15 w/w %, where total amount of surfactant(s), e.g., one or more surfactant, is the total amount of surfactant(s) (e.g., one or more surfactants) including soap if soap is present in the detergent.

In some aspects of the invention, at least one surfactant is selected from the group consisting of anionic surfactant, cationic surfactant and non-ionic surfactant. In one embodiment the ratio of non-ionic surfactant versus anionic and/or cationic surfactant is 1:1, 1:2, 1:3 or 1:4.

In a further embodiment, the detergent composition comprises at least one synthetic surfactant, i.e., an artificial surfactant which is not available from a natural source such as crops, animal fats. In yet a further embodiment, the at least one synthetic surfactant is selected from the list consisting of a synthetic anionic surfactant, synthetic cationic surfactant and synthetic non-ionic surfactant. In a preferred embodiment, said composition comprises at least one anionic surfactant and the amount of said anionic surfactant(s) in said composition is in the range of 2.5 w/w % to 19.6 w/w %, such as in the range of about 2 w/w % to about 30 w/w %, about 2 w/w % to about 20 w/w %, such as in the range of about 5 w/w % to about 20 w/w %, such as about 10 w/w % to about 20 w/w % or such as about 15 w/w % to about 20 w/w %, wherein w/w % means the percent by weight of surfactant in the total weight of detergent solution. If nothing else is mentioned the total amount of surfactant(s) includes soap if one or more soap(s) is present in the detergent. In some aspects the amount of surfactant(s) in the composition of the present invention is in the range of 2 w/w % to 30 w/w %, e.g., in the range of 2 w/w % to 29 w/w %, 2 w/w % to 28 w/w %, 2 w/w % to 27 w/w %, 2 w/w % to 26 w/w %, 2 w/w % to 25 w/w %, 2 w/w % to 24 w/w %, 2 w/w % to 23 w/w %, 2 w/w % to 22 w/w %, 2 w/w % to 21 w/w %, 2 w/w % to 20 w/w %, 2 w/w % to 19 w/w %, 2 w/w % to 18 w/w %, 2 w/w % to 17 w/w %, 2 w/w % to 16 w/w %, 2 w/w % to 15 w/w %, 2 w/w % to 14 w/w %, 2 w/w % to 13 w/w %, 2 w/w % to 12 w/w %, 2 w/w % to 11 w/w %, 2 w/w % to 10 w/w %, 2 w/w % to 9 w/w %, 2 w/w % to 8 w/w %, 2 w/w % to 7 w/w %, 2 w/w % to 6 w/w %, 2 w/w % to 5 w/w %, 2 w/w % to 4 w/w % or 2 w/w % to 3 w/w %, where total amount of surfactant(s), e.g., one or more surfactant, is the total amount of surfactant(s) (e.g., one or more surfactant(s) in the detergent solution.

Surfactants

The detergent composition of the present invention comprises one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The total amount of surfactant(s) is in the range of 3.6 w/w % to 28.5 w/w %, such as 4 w/w % to 25 w/w %, such as, such as 5% to 25%, or 10% to about 20%, or 15% to about 20%, where total amount of surfactant(s), e.g., one or more surfactant, is the total amount of surfactant(s) (e.g., one or more surfactants) in the detergent solution. The surfactant(s) is chosen based on the desired cleaning application, which is laundry.

Anionic Surfactants

In a preferred embodiment of the present invention, the detergent composition comprises at least one anionic surfactant. When included therein the detergent composition, the amount of the anionic surfactant(s) in said composition is in the range of about 2.5 to 20% by weight (w/w %), such as 2.5 w/w % to 19.6 w/w %, for example from about 5 w/w % to about 15 w/w %, such as 10 w/w % to about 15 w/w %. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

In a preferred embodiment, the composition comprises linear alkylbenzene sulfonate (LAS). In one embodiment, the amount of linear alkylbenzene sulfonate (LAS) in the composition is in the range of 1.2 w/w % to 9.6 w/w %, such as 2 w/w % to 9 w/w %, for example 3 w/w % to 7 w/w %, such as 4 w/w % to 6 w/w %, for example 5 w/w % to 6 w/w %.

In some aspects of the present invention provides a detergent composition comprising:
(i) a polypeptide having deoxyribonuclease activity,
(ii) at least one surfactant,
wherein the total amount of surfactant(s) in said composition is in the range of 3.6 w/w % to 28.5 w/w %, optionally in the range of 3 w/w % to 30 w/w %, optionally in the range of 5 w/w % to 20 w/w %, optionally in the range of 10 w/w % to 20 w/w % or optionally in the range of 15 w/w % to 20 w/w %, wherein the composition comprises from about 1.2 w/w % to about 9.6 w/w %, or optionally from about 2 w/w % to about 9 w/w %, or optionally from about 3 w/w % to about 7 w/w %, or optionally from about 4 w/w % to about 6 w/w % or optionally from about 5 w/w % to about 6 w/w % linear alkylbenzene sulfonate (LAS).

In another preferred embodiment, the composition comprises at least one alkyl ethoxysulfate (AEOS). In one embodiment, the amount of said least one alkyl ethoxysulfate (AEOS) in said composition is in the range of 0.7 w/w % to 5.6 w/w %.

Nonionic Surfactants

In one embodiment, the composition comprises at least one nonionic surfactant. When included therein the detergent composition, the at least one nonionic surfactant(s) is in the range of about 1 to 10% by weight (w/w %), such as 1.1 w/w % to 8.8 w/w %, for example from about 1 w/w % to about 9 w/w %, such as 2 w/w % to about 5 w/w %. Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof. In a preferred embodiment, the least one non-ionic surfactant is AEO Biosoft N25-7.

Cationic Surfactants

The detergent composition of the present invention may also include one or more cationic sucfactants. Non-limiting examples of cationic surfactants include alkyldimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, ester quats, and combinations thereof. When included therein the detergent composition, the at least one cationic surfactant(s) is in the range of about 1 to 10% by weight (w/w %), such as 1.1 w/w % to 8.8 w/w %, for example from about 1 w/w % to about 9 w/w %, such as 2 w/w % to about 5 w/w %.

Semipolar Surfactants

The detergent composition of the present invention may also include one or more semipolar surfactants. Non-limiting examples of semipolar surfactants include amine oxides (AO) such as alkyldimethylamineoxide, N-(coco alkyl)-N, N-dimethylamine oxide and N-(tallow-alkyl)-N,N-bis(2-hydroxyethyl)amine oxide, and combinations thereof. Non-limiting examples of zwitterionic surfactants include betaines such as alkyldimethylbetaines, sulfobetaines, and combinations thereof. When included therein the detergent composition, the at least one semipolar surfactant(s) is in the range of about 1 to 10% by weight (w/w %), such as 1.1 w/w % to 8.8 w/w %, for example from about 1 w/w % to about 9 w/w %, such as 2 w/w % to about 5 w/w %.

Hydrotropes

A hydrotrope is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants); however the molecular structure of hydrotropes generally do not favor spontaneous self-aggregation, see, e.g., review by Hodgdon and Kaler, 2007, *Current Opinion in Colloid & Interface Science* 12: 121-128. Hydrotropes do not display a critical concentration above which self-aggregation occurs as found for surfactants and lipids forming miceller, lamellar or other well defined meso-phases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent may contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Builders and Co-Builders

In one embodiment of the present invention, the detergent composition further comprises a builder.

The detergent composition may contain about 0-65% by weight, such as about 5% to about 50% of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg. Any builder and/or co-builder known in the art for use in laundry detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as 2,2'-iminodiethan-l-ol), triethanolamine (TEA, also known as 2,2',2"-nitrilotriethan-1-ol), and (carboxymethyl)inulin (CMI), and combinations thereof.

The detergent composition may also contain 0-50% by weight, such as about 5% to about 30%, of a detergent co-builder. The detergent composition may include include a co-builder alone, or in combination with a builder, for example a zeolite builder. Non-limiting examples of co-builders include homopolymers of polyacrylates or copolymers thereof, such as poly(acrylic acid) (PAA) or copoly (acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra(methylenephosphonic acid) (EDTMPA), diethylenetriaminepentakis(methylenephosphonic acid) (DTMPA or DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N,N-diacetic acid (α-ALDA), serine-N,N-diacetic acid (SEDA), isoserine-N, N-diacetic acid (ISDA), phenylalanine-N,N-diacetic acid (PH DA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA), N-(2-hydroxyethyl)ethylenediamine-N,N',N"-triacetic acid (HEDTA), diethanolglycine (DEG), diethylenetriamine penta(methylenephosphonic acid) (DTPMP), aminotris(methylenephosphonic acid) (ATMP), and combinations and salts thereof. Further exemplary builders and/or co-builders are described in, e.g., WO 2009/102854, U.S. Pat. No. 5,977,053.

Bleaching Systems

The detergent may contain 0-30% by weight, such as about 1% to about 20%, of a bleaching system. Any bleaching system known in the art for use in detergents may be utilized. Suitable bleaching system components include bleaching catalysts, photobleaches, bleach activators, sources of hydrogen peroxide such as sodium percarbonate, sodium perborates and hydrogen peroxide-urea (1:1), preformed peracids and mixtures thereof. Suitable preformed peracids include, but are not limited to, peroxycarboxylic acids and salts, diperoxydicarboxylic acids, perimidic acids and salts, peroxymonosulfuric acids and salts, for example, Oxone (R), and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a per-acid-forming bleach activator. The term bleach activator is meant herein as a compound which reacts with hydrogen peroxide to form a peracid via perhydrolysis. The peracid thus formed constitutes the activated bleach. Suitable bleach activators to be used herein include those belonging to the class of esters, amides, imides or anhydrides. Suitable examples are tetraacetylethylenediamine (TAED), sodium 4-[(3,5,5-trimethylhexanoyl)oxy]benzene-1-sulfonate (ISONOBS), 4-(dodecanoyloxy)benzene-1-sulfonate (LOBS), 4-(decanoyloxy)benzene-1-sulfonate, 4-(decanoyloxy)benzoate (DOBS or DOBA), 4-(nonanoyloxy)benzene-1-sulfonate (NOBS), and/or those disclosed in WO 98/17767. A particular family of bleach activators of interest was disclosed in EP 624154 and particulary preferred in that family is acetyl triethyl citrate (ATC). ATC or a short chain triglyceride like triacetin has the advantage that it is environmentally friendly Furthermore acetyl triethyl citrate and triacetin have good hydrolytical stability in the product upon storage and are efficient bleach activators. Finally, ATC is multifunctional, as the citrate released in the perhydrolysis reaction may function as a builder. Alternatively, the bleaching system may comprise peroxyacids of, for example, the amide, imide, or sulfone type. The bleaching system may also comprise peracids such as 6-(phthalimido)peroxyhexanoic acid (PAP). The bleaching system may also include a bleach catalyst or booster. Some non-limiting examples of bleach catalysts that may be used in the compositions of the present invention include manganese oxalate, manganese acetate, manganese-collagen, cobalt-amine catalysts and manganese triazacyclononane (Mn-TACN) catalysts; particularly preferred are complexes of manganese with 1,4,7-trimethyl-1,4,7-triazacyclononane (Me3-TACN) or 1,2,4,7-tetramethyl-1,4,7-triazacyclononane (Me4-TACN), in particular Me3-TACN, such as the dinuclear manganese complex [(Me3-TACN)Mn(O)3Mn(Me3-TACN)](PF6)2, and [2,2',2"-nitrilotris(ethane-1,2-diylazanylylidene-κN-methanylylidene)triphenolato-κ3O] manganese(III). The bleach catalysts may also be other metal compounds, such as iron or cobalt complexes.

In some embodiments, the bleach component may be an organic catalyst selected from the group consisting of organic catalysts having the following formulae:

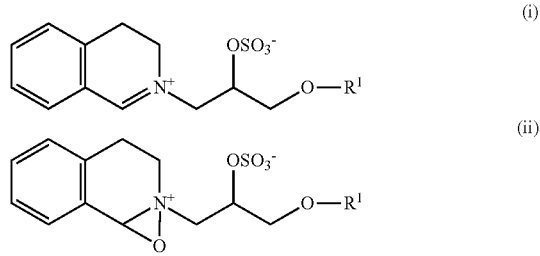

(iii) and mixtures thereof;
wherein each $R^1$ is independently a branched alkyl group containing from 9 to 24 carbons or linear alkyl group containing from 11 to 24 carbons, preferably each $R^1$ is independently a branched alkyl group containing from 9 to 18 carbons or linear alkyl group containing from 11 to 18 carbons, more preferably each $R^1$ is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl. Other exemplary bleaching systems are described, e.g., in WO 2007/087258, WO 2007/087244, WO 2007/087259, EP 1867708 (Vitamin K) and WO 2007/087242. Suitable photobleaches may for example be sulfonated zinc or aluminium phthalocyanines.

Preferably, the bleach component comprises a source of peracid in addition to bleach catalyst, particularly organic bleach catalyst. The source of peracid may be selected from (a) pre-formed peracid; (b) percarbonate, perborate or persulfate salt (hydrogen peroxide source) preferably in combination with a bleach activator; and (c) perhydrolase enzyme and an ester for forming peracid in situ in the presence of water in a textile treatment step.

Polymers

The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or antifoaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly(ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly(oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

Fabric Hueing Agents

The detergent compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO 2005/03274, WO 2005/03275, WO 2005/03276 and EP 1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g., WO 2007/087257 and WO 2007/087243.

Enzymes
Deoxyribonuclease (DNases)

The detergent composition of the present invention comprises a polypeptide having deoxyribonuclease activity (a deoxyribonuclease). The polypeptide having deoxyribonuclease activity is preferably a microbial deoxyribonuclease, such as a bacterial or a fungal deoxyribonuclease.

In one embodiment, the polypeptides having DNase activity are substantially homologous to a bacterial DNase. In the context of the present invention, the term "substantially homologous" denotes a polypeptide having DNase activity which is at least 80%, preferably at least 85%, more preferably at least 90%, more preferably at least 95%, even more preferably at least 96%, 97%, 98%, and most preferably at least 99% identical to the amino acid sequence of a selected bacterial DNase.

In a further embodiment, the polypeptides having DNase activity are substantially homologous to a fungal DNase. In the context of the present invention, the term "substantially homologous" denotes a polypeptide having DNase activity which is at least 80%, preferably at least 85%, more preferably at least 90%, more preferably at least 95%, even more preferably at least 96%, 97%, 98%, and most preferably at least 99% identical to the amino acid sequence of a selected fungal DNase.

In one embodiment of the present invention, the detergent composition comprises at least one polypeptide having deoxyribonuclease activity, which polypeptide is selected from the group consisting of a polypeptide comprising or consisting of the mature polypeptide of SEQ ID NO: 1, a polypeptide comprising or consisting of the amino acid sequence set forth in SEQ ID NO: 2, a polypeptide comprising or consisting of the amino acid sequence set forth in SEQ ID NO: 3, a polypeptide comprising or consisting of the mature polypeptide of SEQ ID NO: 4, a polypeptide comprising or consisting of the mature polypeptide of SEQ ID NO: 5 and a polypeptide comprising or consisting of the mature polypeptide of SEQ ID NO: 6. In a further embodiment, the detergent composition comprises a polypeptide consisting of the amino acid sequence set forth in SEQ ID NO: 2 and a polypeptide consisting of the amino acid sequence set forth in SEQ ID NO: 3.

In one embodiment, the polypeptide contains up to 206 (such as 204) consecutive amino acid residues of the sequence set forth in SEQ ID NO: 1 or SEQ ID NO: 2 (e.g., amino acids 38 to 243 of SEQ ID NO: 1 or amino acids 1 to 206 of SEQ ID NO: 2 or amino acids 1 to 204 of SEQ ID NO: 3), or up to 204 amino acid residues (e.g., amino acids 40 to 243 of SEQ ID NO: 1). In another embodiment, the polypeptide consists of the of the amino acid sequence set forth in SEQ ID NO: 2 or SEQ ID NO: 3. In yet another embodiment, the polypeptide comprises or consists of the consecutive amino acid residues 18 to 205 of SEQ ID NO: 4. In one embodiment, the polypeptide comprises or consists of the consecutive amino acid residues 34 to 142 of SEQ ID NO: 5. In one embodiment, the polypeptide comprises or consists of the consecutive amino acid residues 27 to 136 of SEQ ID NO: 6.

In one embodiment of the present invention, the detergent composition comprises at least one polypeptide having deoxyribonuclease activity, wherein said polypeptide is a polypeptide having at least 80%, at least 85%, at least 90%, at least 91%, at least 92%, at least 93%, at least 94%, at least 95%, at least 96%, at least 97%, at least 98%, or at least 99% sequence identity to the mature polypeptide of SEQ ID NO: 1. In one embodiment, one or more amino acids have been substituted, deleted or inserted with the proviso that the deoxyribonuclease activity is maintained, substantially maintained or increased. In a further embodiment, up to 10 amino acids, e.g., 1, 2, 3, 4, 5, 6, 7, 8, 9, or 10, have been substituted, deleted or inserted.

In one embodiment of the present invention, the detergent composition comprises at least one polypeptide having deoxyribonuclease activity, wherein said polypeptide is a polypeptide having at least 80%, at least 85%, at least 90%, at least 91%, at least 92%, at least 93%, at least 94%, at least 95%, at least 96%, at least 97%, at least 98%, or at least 99% sequence identity to the polypeptide having the amino acid sequence set forth in SEQ ID NO: 2. In one embodiment, one or more amino acids have been substituted, deleted or inserted with the proviso that the deoxyribonuclease activity is maintained, substantially maintained or increased. In a further embodiment, up to 10 amino acids, e.g., 1, 2, 3, 4, 5, 6, 7, 8, 9, or 10, have been substituted, deleted or inserted.

In one embodiment of the present invention, the detergent composition comprises at least one polypeptide having deoxyribonuclease activity, wherein said polypeptide is a polypeptide having at least 80%, at least 85%, at least 90%, at least 91%, at least 92%, at least 93%, at least 94%, at least 95%, at least 96%, at least 97%, at least 98%, or at least 99% sequence identity to the polypeptide having the amino acid sequence set forth in SEQ ID NO: 3. In one embodiment, one or more amino acids have been substituted, deleted or inserted with the proviso that the deoxyribonuclease activity is maintained, substantially maintained or increased. In a further embodiment, up to 10 amino acids, e.g., 1, 2, 3, 4, 5, 6, 7, 8, 9, or 10, have been substituted, deleted or inserted.

In one embodiment of the present invention, the detergent composition comprises at least one polypeptide having deoxyribonuclease activity, wherein said polypeptide is a polypeptide having at least 80%, at least 85%, at least 90%, at least 91%, at least 92%, at least 93%, at least 94%, at least 95%, at least 96%, at least 97%, at least 98%, or at least 99% sequence identity to the mature polypeptide of SEQ ID NO: 4. In one embodiment, one or more amino acids have been substituted, deleted or inserted with the proviso that the deoxyribonuclease activity is maintained, substantially maintained or increased. In a further embodiment, up to 10 amino acids, e.g., 1, 2, 3, 4, 5, 6, 7, 8, 9, or 10, have been substituted, deleted or inserted.

In one embodiment of the present invention, the detergent composition comprises at least one polypeptide having deoxyribonuclease activity, wherein said polypeptide is a polypeptide having at least 80%, at least 85%, at least 90%, at least 91%, at least 92%, at least 93%, at least 94%, at least 95%, at least 96%, at least 97%, at least 98%, or at least 99% sequence identity to the mature polypeptide of SEQ ID NO: 5. In one embodiment, one or more amino acids have been substituted, deleted or inserted with the proviso that the deoxyribonuclease activity is maintained, substantially maintained or increased. In a further embodiment, up to 10 amino acids, e.g., 1, 2, 3, 4, 5, 6, 7, 8, 9, or 10, have been substituted, deleted or inserted.

In one embodiment of the present invention, the detergent composition comprises at least one polypeptide having deoxyribonuclease activity, wherein said polypeptide is a polypeptide having at least 80%, at least 85%, at least 90%, at least 91%, at least 92%, at least 93%, at least 94%, at least 95%, at least 96%, at least 97%, at least 98%, or at least 99% sequence identity to the mature polypeptide of SEQ ID NO: 6. In one embodiment, one or more amino acids have been substituted, deleted or inserted with the proviso that the deoxyribonuclease activity is maintained, substantially maintained or increased. In a further embodiment, up to 10 amino acids, e.g., 1, 2, 3, 4, 5, 6, 7, 8, 9, or 10, have been substituted, deleted or inserted.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for DNase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide having deoxyribonuclease activity may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

In one embodiment, the polypeptide is a fragment of any of the deoxyribonucleases disclosed herein. The fragment may be obtained by truncation of the amino and/or carboxyl terminus of the deoxyribonuclease, for example truncation of the amino and/or carboxyl terminus of a mature polypeptide or domain. The deoxyribonuclease activity of the parent deoxyribonuclease is maintained in the fragment. The deoxyribonuclease activity of the fragment may be slightly lower than the parent deoxyribonuclease in cases where truncation and optional further modification introduces other advantageous properties.

In one embodiment, a fragment contains at least 206 amino acid residues (e.g., amino acids 38 to 243 of SEQ ID NO: 1), at least 205 amino acid residues (e.g., amino acids 39 to 243 of SEQ ID NO: 1), or at least 204 amino acid residues (e.g., amino acids 40 to 243 of SEQ ID NO: 1).

The concentration of the DNase in the wash liquor is typically in the range of 0.00004-100 ppm enzyme protein, such as in the range of 0.00008-100 ppm enzyme protein, in the range of 0.0001-100 ppm enzyme protein, in the range of 0.0002-100 ppm enzyme protein, in the range of 0.0004-100 ppm enzyme protein, in the range of 0.0008-100 ppm enzyme protein, in the range of 0.001-100 ppm enzyme protein, 0.01-100 ppm enzyme protein, preferably 0.05-50 ppm enzyme protein, more preferably 0.1-50 ppm enzyme protein, more preferably 0.1-30 ppm enzyme protein, more preferably 0.5-20 ppm enzyme protein, and most preferably 0.5-10 ppm enzyme protein. In one embodiment, the concentration of the polypeptide having deoxyribonuclease activity in a wash dose of said detergent composition is within the range of 0.001 ppm to 100 ppm.

The DNase of the present invention may be added to a detergent composition in an amount corresponding to at least 0.002 mg of DNase protein, such as at least 0.004 mg of DNase protein, at least 0.006 mg of DNase protein, at least 0.008 mg of DNase protein, at least 0.01 mg of DNase protein, at least 0.02 mg of DNase protein, at least 0.05 mg of DNase protein, at least 0.1 mg of protein, at least 0.2 mg of DNase protein, preferably at least 0.01 mg of protein, preferably at least 0.02 mg of protein, preferably at least 0.5 mg of protein, preferably at least 1 mg of protein, more preferably at least 10 mg of protein, even more preferably at least 15 mg of protein, most preferably at least 20 mg of protein, and even most preferably at least 25 mg of protein. Thus, the detergent composition may comprise at least 0.00008% DNase protein, preferably at least 0.002%, 0.003%, 0.004%, 0.005%, 0.006%, 0.008%, 0.01%, 0.02%, 0.03%, 0.05%, 0.1%, 0.2%, 0.3%, 0.4%, 0.6%, 0.7%, 0.8%, 0.9% or 1.0% of DNase protein.

In some aspects, the present invention provides a detergent composition comprising:

(i) a polypeptide having deoxyribonuclease activity, wherein the concentration of the DNase in said composition is at least 0.002 mg of active DNase protein per litre of detergent composition, such as at least 0.004 mg of active DNase protein, at least 0.006 mg of active DNase protein, at least 0.008 mg of active DNase protein, or such as at least 0.01 mg of active DNase protein, at least 0.02 mg of active DNase protein, at least 0.05 mg of active DNase protein, at least 0.1 mg of active DNase protein, at least 0.2 mg of active DNase protein or at least 0.5 mg of active DNase protein, e.g., the detergent composition may comprise at least 0.00008% DNase protein, preferably at least 0.002%, 0.003%, 0.004%, 0.005%, 0.006%, 0.008%, 0.01%, 0.02%, 0.03%, 0.05%, 0.1%, 0.2%, 0.3%, 0.4%, 0.6%, 0.7%, 0.8%, 0.9% or 1.0% of DNase protein, and (ii) at least one surfactant, wherein the total amount of surfactant(s) in said composition is in the range of 3.6 w/w % to 28.5 w/w %, optionally in the range of 3 w/w % to 30 w/w %, optionally in the range of 5 w/w % to 20 w/w %, optionally in the range of 10 w/w % to 20 w/w % or optionally in the range of 15 w/w % to 20 w/w %, optionally in the range of w/w % 10 to 15 w/w % or optionally below 20 w/w %, such as below 15 w/w % but more than 0 w/w %.

In one aspect, at least one surfactant is LAS.

The DNase of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO 92/19709 and WO 92/19708.

A polypeptide of the present invention may also be incorporated in the detergent formulations disclosed in WO 97/07202, which is hereby incorporated by reference.

The detergent composition of the present invention may comprise one or more additional enzymes such as a protease, lipase, cutinase, an amylase, carbohydrase, cellulase, pectinase, mannanase, arabinase, galactanase, xylanase, oxidase, e.g., a laccase, and/or peroxidase.

In general, the properties of the selected enzyme(s) should be compatible with the selected detergent, (i.e., pH-optimum, compatibility with other enzymatic and non-enzymatic ingredients, etc.), and the enzyme(s) should be present in effective amounts. In a preferred embodiment, the detergent composition comprises a protease.

Cellulases

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO 99/01544.

Other cellulases are endo-beta-1,4-glucanase enzyme having a sequence of at least 97% identity to the amino acid sequence of position 1 to position 773 of SEQ ID NO:2 of WO 2002/099091 or a family 44 xyloglucanase, which a xyloglucanase enzyme having a sequence of at least 60% identity to positions 40-559 of SEQ ID NO: 2 of WO 01/62903.

Commercially available cellulases include Celluzyme™, and Carezyme™ (Novozymes A/S) Carezyme Premium™ (Novozymes A/S), Celluclean™ (Novozymes A/S), Celluclean Classic™ (Novozymes A/S), Cellusoft (Novozymes A/S), Whitezyme™ (Novozymes A/S), Clazinase™, and Puradax HA™ (Genencor International Inc.), and KAC-500 (B)™ (Kao Corporation).

Proteases

Suitable proteases include those of bacterial, fungal, plant, viral or animal origin, e.g., vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from, e.g., family M4 or other metalloprotease such as those from M5, M7 or M8 families.

The term "subtilases" refers to a sub-group of serine protease according to Siezen et al., 1991, *Protein Engng.* 4: 719-737 and Siezen et al., 1997, *Protein Science* 6: 501-523. Serine proteases are a subgroup of proteases characterized by having a serine in the active site, which forms a covalent adduct with the substrate. The subtilases may be divided into 6 sub-divisions, i.e., the Subtilisin family, the Thermitase family, the Proteinase K family, the Lantibiotic peptidase family, the Kexin family and the Pyrolysin family.

Examples of subtilases are those obtained from *Bacillus* such as *Bacillus lentus, B. alkalophilus, B. subtilis, B. amyloliquefaciens, Bacillus pumilus* and *Bacillus gibsonii* described in U.S. Pat. No. 7,262,042 and WO 2009/021867, and subtilisin *lentus*, subtilisin *Novo*, subtilisin *Carlsberg*, *Bacillus licheniformis*, subtilisin BPN', subtilisin 309, subtilisin 147 and subtilisin 168 described in WO 89/06279 and protease PD138 described in (WO 93/18140). Other useful proteases may be those described in WO 92/175177, WO 01/16285, WO 02/026024 and WO 02/016547. Examples of trypsin-like proteases are trypsin (e.g., of porcine or bovine origin) and the *Fusarium* protease described in WO 89/06270, WO 94/25583 and WO 2005/040372, and the chymotrypsin proteases obtained from *Cellumonas* described in WO 2005/052161 and WO 2005/052146.

A further preferred protease is the alkaline protease from *Bacillus lentus* DSM 5483, as described for example in WO 95/23221, and variants thereof which are described in WO 92/21760, WO 95/23221, EP 1921147 and EP 1921148.

Examples of metalloproteases are the neutral metalloprotease as described in WO 2007/044993 (Genencor Int.) such as those obtained from *Bacillus amyloliquefaciens*.

Examples of useful proteases are the protease variants described in: WO 92/19729, WO 96/034946, WO 98/20115, WO 98/20116, WO 99/11768, WO 01/44452, WO 03/006602, WO 2004/03186, WO 2004/041979, WO 2007/006305, WO 2011/036263, WO 2011/036264, especially the protease variants with alterations in one or more of the following positions: 3, 4, 9, 15, 27, 36, 57, 68, 76, 87, 95, 96, 97, 98, 99, 100, 101, 102, 103, 104, 106, 118, 120, 123, 128, 129, 130, 160, 167, 170, 194, 195, 199, 205, 206, 217, 218, 222, 224, 232, 235, 236, 245, 248, 252 and 274 corresponding to the positions in BPN', i.e., BPN' numbering. More preferred the protease variants are variants of a subtilase variants which comprise one or more of the mutations: S3T, V4I, S9R, A15T, K27R, *36D, V68A, N76D, N87S,R, *97E, A98S, S99G,D,A, S99AD, S101G,M,R S103A, V104I,Y,N, S106A, G118V,R, H120D,N, N123S, S128L, P129Q, S130A, G160D, Y167A, R170S, A194P, G195E, V199M, V205I, L217D, N218D, M222S, A232V, K235L, Q236H, Q245R, N252K, T274A (using BPN' numbering). The protease variants are preferably variants of the *Bacillus Lentus* protease (Savinase®) shown in SEQ ID NO: 1 of WO 2016/001449 and in SEQ ID NO: 7, or of the *Bacillus amylolichenifaciens* protease (BPN') shown in SEQ ID NO: 2 of WO 2016/001449. The protease variants preferably have at least 80% sequence identity to SEQ ID NO: 7 or SEQ ID NO: 1 or 2 of WO 2016/001449. The term "BPN' numbering" has it common meaning within the protease field and includes the numbering according to the alignment of Savinase and BPN' as shown in WO 91/00345. The amino acid preceding the position is the amino acid present in sequence of the protease Savinase, e.g., shown in SEQ ID NO: 1 of WO 2016/001449 (or SEQ ID NO: 7 of the present invention) it is clear to the person skilled in the art that the amino acid to be replaced or deleted can be any amino acid and depends on the parent protease.

A protease variant comprising a substitution at one or more positions corresponding to positions 171, 173, 175, 179, or 180 of SEQ ID NO: 1 of WO 2004/067737, wherein said protease variant has a sequence identity of at least 75% but less than 100% to SEQ ID NO: 1 of WO 2004/067737.

Suitable commercially available protease enzymes include those sold under the trade names: Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Blaze®, Blaze Evity® 100T, Blaze Evity® 125T, Blaze Evity® 150T, Neutrase®, Everlase® and Esperase (Novozymes A/S), those sold under the tradename Maxatase®, Maxacal®, Maxapem®, Purafect Ox®, Purafect OxP®, Puramax®, FN2®, FN3®, FN4®, Excellase®, Excellenz P1000™, Excellenz P1250™, Eraser®, Preferenz P100™, Purafect Prime®, Preferenz P110™, Effectenz P1000™, Purafect®™, Effectenz P1050™, Purafect Ox®™, Effectenz P2000™, Purafast®, Properase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

In one embodiment of the invention, the inventive detergent composition is formulated with a protease, which is of animal, vegetable or microbial origin. The protease is chemically modified or protein engineered. The protease can be a serine protease or a metalloprotease, preferably an alkaline microbial protease or a trypsin-like protease.

In one embodiment of the invention, the protease is selected from the group consisting of *Bacillus*, e.g., subtilisin *Novo*, subtilisin *Carlsberg*, subtilisin 309, subtilisin 147, subtilisin 168, trypsin of bovine origin, trypsin of porcine origin and *Fusarium* protease. The protease can have at least 90%, such as at least 95%, sequence identity to SEQ ID NO: 7. In one embodiment, the protease has at least 90% identity to the amino acid sequence of SEQ ID NO: 10 or a variant thereof with substitutions in one or more of the following positions: 27, 36, 57, 76, 87, 97, 101, 104, 120, 123, 167, 170, 194, 206, 218, 222, 224, 235, and 274, preferably the variant is an alkaline protease having at least 90% identity to the amino acid sequence of SEQ ID NO: 7 with the following substitution: M222S, or substitutions N76D+G195E.

Lipases and Cutinases

Suitable lipases and cutinases include those of bacterial or fungal origin. Chemically modified or protein engineered mutant enzymes are included. Examples include lipase from *Thermomyces*, e.g., from *T. lanuginosus* (previously named *Humicola lanuginosa*) as described in EP 258068 and EP 305216, cutinase from *Humicola*, e.g., *H. insolens* (WO 96/13580), lipase from strains of *Pseudomonas* (some of these now renamed to *Burkholderia*), e.g., *P. alcaligenes* or *P. pseudoalcaligenes* (EP 218272), *P. cepacia* (EP 331376), *P.* sp. strain SD705 (WO 95/06720 & WO 96/27002), *P. wisconsinensis* (WO 96/12012), GDSL-type *Streptomyces* lipases (WO 2010/065455), cutinase from *Magnaporthe grisea* (WO 2010/107560), cutinase from *Pseudomonas mendocina* (U.S. Pat. No. 5,389,536), lipase from *Thermobifida fusca* (WO 2011/084412), *Geobacillus stearothermophilus* lipase (WO 2011/084417), lipase from *Bacillus subtilis* (WO 2011/084599), and lipase from *Streptomyces griseus* (WO 2011/150157) and *S. pristinaespiralis* (WO 2012/137147).

Other examples are lipase variants such as those described in EP 407225, WO 92/05249, WO 94/01541, WO 94/25578, WO 95/14783, WO 95/30744, WO 95/35381, WO 95/22615, WO 96/00292, WO 97/04079, WO 97/07202, WO 00/34450, WO 00/60063, WO 01/92502, WO 2007/87508 and WO 2009/109500.

Preferred commercial lipase products include include Lipolase™, Lipex™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g., acyltransferases with homology to Candida antarctica lipase A (WO 2010/111143), acyltransferase from *Mycobacterium smegmatis* (WO 2005/056782), perhydrolases from the CE 7 family (WO 2009/67279), and variants of the *M. smegmatis* perhydrolase in particular the S54V variant used in the commercial product Gentle Power Bleach from Huntsman Textile Effects Pte Ltd (WO 2010/100028).

Amylases

Suitable amylases which can be used together with the enzyme of the invention may be an alpha-amylase or a glucoamylase and may be of bacterial or fungal origin. Chemically modified or protein engineered mutants are included. Amylases include, for example, alpha-amylases obtained from Bacillus, e.g., a special strain of Bacillus licheniformis, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase obtained from B. amyloliquefaciens shown in SEQ ID NO: 6 of WO 2006/066594 and residues 36-483 of the B. licheniformis alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase obtained from B. amyloliquefaciens shown in SEQ ID NO: 6 of WO 2006/066594 and residues 36-483 of SEQ ID NO: 4 are those having the substitutions:

M 197T;
H156Y+A181T+N190F+A209V+Q264S; or
G48A+T49I+G107A+H156Y+A181T+N190F+I201F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/23873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/23873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 08/153815, SEQ ID NO: 10 in WO 01/66712 or variants thereof having 90% sequence identity to SEQ ID NO: 2 of WO 2008/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 2009/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E, R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;
N128C+K178L+T182G+F202Y+Y305R+D319T+G475K;
S125A+N128C+K178L+T182G+Y305R+G475K; or
S125A+N128C+T131I+T165I+K178L+T182G+Y305R+G475K, wherein the variants are C-terminally truncated and optionally further comprises a substitution at position 243 and/or a deletion at position 180 and/or position 181.

Other suitable amylases are the alpha-amylase having SEQ ID NO: 12 in WO 01/66712 or a variant having at least 90% sequence identity to SEQ ID NO: 12. Preferred amylase variants are those having a substitution, a deletion or an insertion in one of more of the following positions of SEQ ID NO: 12 in WO 01/66712: R28, R118, N174, R181, G182, D183, G184, G186, W189, N195, M202, Y298, N299, K302, S303, N306, R310, N314, R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO 2011/098531, WO 2013/001078 and WO 2013/001087.

Commercially available amylases are Duramyl™, Termamyl™, Fungamyl™, Stainzyme™, Stainzyme Plus™, Natalase™, Liquozyme X and BAN™ (from Novozymes A/S), and Rapidase™, Purastar™/Effectenz™, Powerase and Preferenz S100 (from Genencor International Inc./DuPont).

Peroxidases/Oxidases

A peroxidase according to the invention is a peroxidase enzyme comprised by the enzyme classification EC 1.11.1.7, as set out by the Nomenclature Committee of the International Union of Biochemistry and Molecular Biology (IUBMB), or any fragment obtained therefrom, exhibiting peroxidase activity.

Suitable peroxidases include those of plant, bacterial or fungal origin. Chemically modified or protein engineered mutants are included. Examples of useful peroxidases include peroxidases from *Coprinopsis*, e.g., from *C. cinerea* (EP 179,486), and variants thereof as those described in WO 93/24618, WO 95/10602, and WO 98/15257.

A peroxidase according to the invention also includes a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions.

In an embodiment, the haloperoxidase of the invention is a chloroperoxidase. Preferably, the haloperoxidase is a vanadium haloperoxidase, i.e., a vanadate-containing haloperoxidase. In a preferred method of the present invention the vanadate-containing haloperoxidase is combined with a source of chloride ion.

Haloperoxidases have been isolated from many different fungi, in particular from the fungus group dematiaceous hyphomycetes, such as *Caldariomyces*, e.g., *C. fumago*, *Alternaria*, *Curvularia*, e.g., *C. verruculosa* and *C. inaequalis*, *Drechslera*, *Ulocladium* and *Botrytis*.

Haloperoxidases have also been isolated from bacteria such as *Pseudomonas*, e.g., *P. pyrrocinia* and *Streptomyces*, e.g., *S. aureofaciens*.

In a preferred embodiment, the haloperoxidase is derivable from *Curvularia* sp., in particular *Curvularia verruculosa* or *Curvularia inaequalis*, such as *C. inaequalis* CBS 102.42 as described in WO 95/27046; or *C. verruculosa* CBS 147.63 or *C. verruculosa* CBS 444.70 as described in WO 97/04102; or from *Drechslera hartlebii* as described in WO 01/79459, *Dendtyphiella salina* as described in WO 01/79458, *Phaeotrichoconis crotalarie* as described in WO 01/79461, or *Geniculosporium* sp. as described in WO 01/79460.

An oxidase according to the invention include, in particular, any laccase enzyme comprised by the enzyme classification EC 1.10.3.2, or any fragment obtained therefrom exhibiting laccase activity, or a compound exhibiting a similar activity, such as a catechol oxidase (EC 1.10.3.1), an o-aminophenol oxidase (EC 1.10.3.4), ora bilirubin oxidase (EC 1.3.3.5).

Preferred laccase enzymes are enzymes of microbial origin. The enzymes may be obtained from plants, bacteria or fungi (including filamentous fungi and yeasts).

Suitable examples from fungi include a laccase derivable from a strain of *Aspergillus*, *Neurospora*, e.g., *N. crassa*, *Podospora*, *Botrytis*, *Collybia*, *Fomes*, *Lentinus*, *Pleurotus*, *Trametes*, e.g., *T. villosa* and *T. versicolor*, *Rhizoctonia*, e.g., *R. solani*, *Coprinopsis*, e.g., *C. cinerea*, *C. comatus*, *C. friesii*, and *C. plicatilis*, *Psathyrella*, e.g., *P. condelleana*, *Panaeolus*, e.g., *P. papilionaceus*, *Myceliophthora*, e.g., *M. thermophila*, *Schytalidium*, e.g., *S. thermophilum*, *Polyporus*, e.g., *P. pinsitus*, *Phlebia*, e.g., *P. radiata* (WO 92/01046), or *Coriolus*, e.g., *C. hirsutus* (JP 2238885).

Suitable examples from bacteria include a laccase derivable from a strain of *Bacillus*.

A laccase obtained from *Coprinopsis* or *Myceliophthora* is preferred; in particular a laccase obtained from *Coprinopsis cinerea*, as disclosed in WO 97/08325; or from *Myceliophthora thermophila*, as disclosed in WO 95/33836.

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

Other Materials

Any detergent components known in the art for use in detergents may also be utilized. Other optional detergent components include anti-corrosion agents, anti-shrink agents, anti-soil redeposition agents, anti-wrinkling agents, bactericides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in detergents may be utilized. The choice of such ingredients is well within the skill of the artisan.

Dispersants

The detergent compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents

The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent

The detergent compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2.2'-disulfonate, 4,4'-bis-(2-anilino-4-(N-methyl-N-2-hydroxy-ethylamino)-s-triazin-6-ylamino) stilbene-2,2'-disulfonate, 4,4'-bis-(4-phenyl-1,2,3-triazol-2-yl)stilbene-2,2'-disulfonate and sodium 5-(2H-naphtho[1,2-d][1,2,3]triazol-2-yl)-2-[(E)-2-phenylvinyl]benzenesulfonate.

Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Tinopal CBS-X is a 4.4'-bis-(sulfostyryl)-biphenyl disodium salt also known as Disodium Distyrylbiphenyl Disulfonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins.

Suitable fluorescent brightener levels include lower levels of from about 0.01, from 0.05, from about 0.1 or even from about 0.2 wt % to upper levels of 0.5 or even 0.75 wt %.

Soil Release Polymers

The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore random graft co-polymers are suitable soil release polymers. Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose derivatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents

The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Rheology Modifiers

The detergent compositions of the present invention may also include one or more rheology modifiers, structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Formulation of Detergent Products

The detergent composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid. In one embodiment of the present invention, the detergent composition is in a solid form.

Pouches can be configured as single or multicompartments. It can be of any form, shape and material which is suitable for hold the composition, e.g., without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blended compositions comprising hydrolytically degradable and water soluble polymer blends such as polylactide and polyvinyl alcohol (known under the Trade reference M8630 as sold by Mono-Sol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids: US 2009/0011970.

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent. In one embodiment, the detergent composition comprises a solvent.

A liquid or gel detergent may be non-aqueous.

The detergent composition may be formulated as a bar, a homogenous tablet, and a tablet having two or more layers, a pouch having one or more compartments, a regular or compact powder, a granule, a paste, a gel, or a regular, compact or concentrated liquid. The detergent composition can be a liquid detergent, a powder detergent or a granule detergent.

The invention further concerns a liquid detergent composition comprising a surfactant and a detergent builder in a total concentration of at least 3% by weight, and a detergent enzyme containing microcapsule, wherein the membrane of the microcapsule is produced by cross-linking of a poly-branched polyamine having a molecular weight of more than 1 kDa. The inventors have found, that encapsulating enzymes in a microcapsule with a semipermeable membrane of the invention, and having a water activity inside these capsules (prior to addition to the liquid detergent) higher than in the liquid detergent, the capsules will undergo a (partly) collapse when added to the detergent (water is oozing out), thus leaving a more concentrated and more viscous enzyme containing interior in the capsules. The collapse of the membrane may also result in a reduced permeability. This can be further utilized by addition of stabilizers/polymers, especially ones that are not permeable through the membrane. The collapse and resulting increase in viscosity will reduce/hinder the diffusion of hostile components (e.g., surfactants or sequestrants) into the capsules, and thus increase the storage stability of the enzyme in the liquid detergent. Components in the liquid detergent that are sensitive to the enzyme (e.g., components that act as substrate for the enzyme) are also protected against degradation by the enzyme. During wash the liquid detergent is diluted by water, thus increasing the water activity. Water will now diffuse into the capsules (osmosis). The capsules will swell and the membrane will either become permeable to the enzyme so they can leave the capsules, or simply burst and in this way releasing the enzyme. The concept is very efficient in stabilizing the enzymes against hostile components in liquid detergent, and vice versa also protects enzyme sensitive components in the liquid detergent from enzymes.

Examples of detergent components which are sensitive to, and can be degraded by, enzymes include (relevant enzyme in parenthesis): xanthan gum (xanthanase), polymers with ester bonds (lipase), hydrogenated castor oil (lipase), perfume (lipase), methyl ester sulfonate surfactants (lipase), cellulose and cellulose derivatives (e.g., CMC) (cellulase), and dextrin and cyclodextrin (amylase).

Also, sensitive detergent ingredients can be encapsulated, and thus stabilized, in the microcapsules of the invention. Sensitive detergent ingredients are prone to degradation during storage. Such detergent ingredients include bleaching compounds, bleach activators, perfumes, polymers, builder, surfactants, etc.

Generally, the microcapsules of the invention can be used to separate incompatible components/compounds in detergents.

Addition of the microcapsules to detergents can be used to influence the visual appearance of the detergent product, such as an opacifying effect (small microcapsules) or an effect of distinctly visible particles (large microcapsules). The microcapsules may also be colored.

The microcapsules can be used to reduce the enzyme dust levels during handling and processing of enzyme products.

Unless otherwise indicated, all percentages are indicated as percent by weight (% w/w) throughout the application.

Microcapsule: The microcapsules are typically produced by forming water droplets into a continuum that is non-miscible with water—i.e., typically by preparing a water-in-oil emulsion—and subsequently formation of the membrane by interfacial polymerization via addition of a cross-linking agent. After eventual curing the capsules can be harvested and further rinsed and formulated by methods known in the art. The capsule formulation is subsequently added to the detergent.

The payload, the major membrane constituents and eventual additional component that are to be encapsulated are found in the water phase. In the continuum is found components that stabilize the water droplets towards coalescence (emulsifiers, emulsion stabilizers, surfactants etc.) and the cross linking agent is also added via the continuum.

The emulsion can be prepared be any methods known in the art, e.g., by mechanical agitation, dripping processes, membrane emulsification, microfluidics, sonication etc. In some cases simple mixing of the phases automatically will result in an emulsion, often referred to as self-emulsification. Using methods resulting in a narrow size distribution is an advantage.

The cross-linking agent(s) is typically subsequently added to the emulsion, either directly or more typically by preparing a solution of the crosslinking agent in a solvent which is soluble in the continuous phase. The emulsion and cross-linking agent or solution hereof can be mixed by conventional methods used in the art, e.g., by simple mixing or by carefully controlling the flows of the emulsion and the cross-linking agent solution through an in-line mixer.

In some cases, curing of the capsules is needed to complete the membrane formation. Curing is often simple stirring of the capsules for some time to allow the interfacial polymerization reaction to end. In other cases the membrane formation can be stopped by addition of reaction quencher.

The capsules may be post modified, e.g., by reacting components onto the membrane to hinder or reduce flocculation of the particles in the detergent as described in WO 99/01534.

The produced capsules can be isolated or concentrated by methods known in the art, e.g., by filtration, centrifugation, distillation or decantation of the capsule dispersion.

The resulting capsules can be further formulated, e.g., by addition of surfactants to give the product the desired properties for storage, transport and later handling and addition to the detergent. Other microcapsule formulation agents include rheology modifiers, biocides (e.g., Proxel), acid/base for adjustment of pH (which will also adjust inside the microcapsules), and water for adjustment of water activity.

The capsule forming process may include the following steps:
Preparation of the initial water and oil phase(s),
Forming a water-in-oil emulsion,
Membrane formation by interfacial polymerization,
Optional post modification,
Optional isolation and/or formulation,
Addition to detergent.

The process can be either a batch process or a continuous or semi-continuous process.

A microcapsule according to the invention is a small aqueous sphere with a uniform membrane around it. The material inside the microcapsule is referred to as the core, internal phase, or fill, whereas the membrane is sometimes called a shell, coating, or wall. The microcapsules of the invention have diameters between 0.5 µm and 2 millimeters. Preferably, the mean diameter of the microcapsules is in the range of 1 µm to 1000 µm, more preferably in the range of 5 µm to 500 µm, even more preferably in the range of 10 µm to 500 µm, even more preferably in the range of 50 µm to 500 µm, and most preferably in the range of 50 µm to 200 µm. Alternatively, the diameter of the microcapsules is in the range of 0.5 µm to 30 µm; or in the range of 1 µm to 25 µm. The diameter of the microcapsule is measured in the oil phase after polymerization is complete. The diameter of the capsule may change depending on the water activity of the surrounding chemical environment.

Microencapsulation of enzymes, as used in the present invention, may be carried out by interfacial polymerization, wherein the two reactants in a polymerization reaction meet at an interface and react rapidly. The basis of this method is a reaction of a polyamine with an acid derivative, usually an acid halide, acting as a crosslinking agent. The polyamine is preferably substantially water-soluble (when in free base form). Under the right conditions, thin flexible membranes form rapidly at the interface. One way of carrying out the polymerization is to use an aqueous solution of the enzyme and the polyamine, which are emulsified with a non-aqueous solvent (and an emulsifier), and a solution containing the acid derivative is added. An alkaline agent may be present in the enzyme solution to neutralize the acid formed during the reaction. Polymer (polyamide) membranes form instantly at the interface of the emulsion droplets. The polymer membrane of the microcapsule is typically of a cationic nature, and thus bind/complex with compounds of an anionic nature.

The diameter of the microcapsules is determined by the size of the emulsion droplets, which is controlled, for example by the stirring rate.

Emulsion: An emulsion is a temporary or permanent dispersion of one liquid phase within a second liquid phase. The second liquid is generally referred to as the continuous phase. Surfactants are commonly used to aid in the formation and stabilization of emulsions. Not all surfactants are equally able to stabilize an emulsion. The type and amount of a surfactant needs to be selected for optimum emulsion utility especially with regard to preparation and physical stability of the emulsion, and stability during dilution and further processing. Physical stability refers to maintaining an emulsion in a dispersion form. Processes such as coalescence, aggregation, adsorption to container walls, sedimentation and creaming, are forms of physical instability, and should be avoided. Examples of suitable surfactants are described in WO 97/24177, pages 19-21; and in WO 99/01534.

Emulsions can be further classified as either simple emulsions, wherein the dispersed liquid phase is a simple homogeneous liquid, or a more complex emulsion, wherein the dispersed liquid phase is a heterogeneous combination of liquid or solid phases, such as a double emulsion or a multiple-emulsion. For example, a water-in-oil double emulsion or multiple emulsion may be formed wherein the water phase itself further contains an emulsified oil phase; this type of emulsion may be specified as an oil-in-water-in oil (o/w/o) emulsion. Alternatively, a water-in-oil emulsion may be formed wherein the water phase contains a dispersed solid phase often referred to as a suspension-emulsion. Other more complex emulsions can be described. Because of the inherent difficulty in describing such systems, the term emulsion is used to describe both simple and more complex emulsions without necessarily limiting the form of the emulsion or the type and number of phases present Polyamine: The rigidity/flexibility and permeability of the membrane is mainly influenced by the choice of polyamine. The polyamine according to the invention is a polybranched polyamine. Each branch, preferably ending with a primary amino group serves as a tethering point in the membrane network, thereby giving the favorable properties of the invention. A polybranched polyamine according to the present invention is a polyamine having more than two branching points and more than two reactive amino groups (capable of reacting with the crosslinking agent, i.e., primary and secondary amino groups). The polybranched polyamine is used as starting material when the emulsion is prepared— it is not formed in situ from other starting materials. To obtain the attractive properties of the invention, the polybranched structure of the polyamine must be present as starting material.

There is a close relation between number of branching points and number of primary amines, since primary amines will always be positioned at the end of a branch: A linear amine can only contain two primary amines. For each branching point hypothetically introduced in such a linear di-amine will allow one or more primary amine(s) to be introduced at the end of the introduced branch(es). In this context we understand the primary amino group as part of the branch, i.e., the endpoint of the branch. For example, we consider both tris(2-aminoethyl)amine and 1,2,3-propanetri-amine as molecules having one branching point. For the invention the polyamine has at least four primary amines. Branching points can be introduced from an aliphatic hydrocarbon chain as in the previously stated examples or from unsaturated carbon bonds, such as in, e.g., 3,3'-diaminobenzidine, or from tertiary amino groups, such as in N,N,N',N'-tetrakis-(2-aminoethyl)ethylenediamine.

In addition to the number of branching points, we have found that the compactness of the reactive amino groups is of high importance. A substance such as, e.g., N,N,N',N'-tetrakis-(12-aminododecyl)ethylenediamine would not be suitable. Neither would a peptide or protein, such as an enzyme, be suitable for membrane formation. Thus, the polybranched polyamine is not a peptide or protein.

In an embodiment, the reactive amino groups constitute at least 15% of the molecular weight of the polybranched polyamine, such as more than 20%, or more than 25%. Preferably, the molecular weight of the polybranched polyamine is at least 1 kDa; more preferably, the molecular weight of the polybranched polyamine is at least 1.3 kDa.

In a preferred embodiment, the polybranched polyamine is a polyethyleneimine (PEI), and modifications thereof, having more than two branching points and more than two reactive amino groups; wherein the reactive amino groups constitute at least 15% of the molecular weight of the PEI, such as more than 20%, or more than 25%. Preferably, the molecular weight of the PEI is at least 1 kDa.

Combinations of different polybranched polyamines may be used for preparing the microcapsule according to the invention.

The advantageous properties (e.g., enzyme storage stability, reduced enzyme leakage, reduced in-flux of detergent ingredients) of the microcapsule of the invention may be improved by adding one or more small amines with a molecular weight of less than 1 kDa. The small amine is preferably substantially water-soluble (when in free base form) and can be a material such as ethylene diamine, hexamethylene diamine, hexane diamine, diethylene tetramine, ethylene tetramine, diamino benzene, piperazine, tetramethylene pentamine or, preferably, diethylene triamine (DETA). The small amines may be added in an amount of up to 50%, preferably up to 40%, up to 30%, up to 20%, up to 10%, or up to 5%, by weight of the total content of small amine and polybranched polyamine, when preparing the microcapsule of the invention.

Crosslinking agent: The crosslinking agent as used in the present invention is a molecule with at least two groups/sites capable of reacting with amines to form covalent bonds.

The crosslinking agent is preferably oil soluble and can be in the form of an acid anhydride or acid halide, preferably an acid chloride. For example, it can be adipoyl chloride, sebacoyl chloride, dodecanedioc acid chloride, phthaloyl chloride, terephthaloyl chloride, isophthaloyl chloride, or trimesoyl chloride; but preferably, the crosslinking agent is terephthaloyl chloride or trimesoyl chloride.

Liquid Detergent Composition

In one embodiment of the present invention, the detergent is in a liquid form. The liquid detergent composition may comprise a microcapsule, and thus form part of, any detergent composition in any form, such as liquid and powder detergents, and soap and detergent bars.

In one embodiment, the invention is directed to liquid detergent compositions comprising a microcapsule, as described above, in combination with one or more additional cleaning composition components.

The microcapsule, as described above, may be added to the liquid detergent composition in an amount corresponding to from 0.0001% to 5% (w/w) active enzyme protein (AEP); preferably from 0.001% to 5%, more preferably from 0.005% to 5%, more preferably from 0.005% to 4%, more preferably from 0.005% to 3%, more preferably from 0.005% to 2%, even more preferably from 0.01% to 2%, and most preferably from 0.01% to 1% (w/w) active enzyme protein.

The liquid detergent composition has a physical form, which is not solid (or gas). It may be a pourable liquid, a paste, a pourable gel or a non-pourable gel. It may be either isotropic or structured, preferably isotropic. It may be a formulation useful for washing in automatic washing machines or for hand washing. It may also be a personal care product, such as a shampoo, toothpaste, or a hand soap.

The liquid detergent composition may be aqueous, typically containing at least 20% by weight and up to 95% water, such as up to 70% water, up to 50% water, up to 40% water, up to 30% water, or up to 20% water. Other types of liquids, including without limitation, alkanols, amines, diols, ethers and polyols may be included in an aqueous liquid detergent. An aqueous liquid detergent may contain from 0-30% organic solvent. A liquid detergent may even be non-aqueous, wherein the water content is below 10%, preferably below 5%.

Detergent ingredients can be separated physically from each other by compartments in water dissolvable pouches. Thereby negative storage interaction between components can be avoided. Different dissolution profiles of each of the compartments can also give rise to delayed dissolution of selected components in the wash solution.

The detergent composition may take the form of a unit dose product. A unit dose product is the packaging of a single dose in a non-reusable container. It is increasingly used in detergents for laundry. A detergent unit dose product is the packaging (e.g., in a pouch made from a water soluble film) of the amount of detergent used for a single wash.

Pouches can be of any form, shape and material which is suitable for holding the composition, e.g., without allowing the release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be a blend compositions comprising hydrolytically degradable and water soluble polymer blends such as polyactide and polyvinyl alcohol (known under the Trade reference M8630 as sold by Chris Craft In. Prod. Of Gary, Ind., US) plus plasticizers like glycerol, ethylene glycerol, Propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids (see, e.g., US 2009/0011970).

The choice of detergent components may include, for textile care, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

Laundry Soap Bars

The DNase of the invention may be added to laundry soap bars and used for hand washing laundry, fabrics and/or textiles. The term laundry soap bar includes laundry bars, soap bars, combo bars, syndet bars and detergent bars. The types of bar usually differ in the type of surfactant they contain, and the term laundry soap bar includes those containing soaps from fatty acids and/or synthetic soaps. The laundry soap bar has a physical form which is solid and not a liquid, gel or a powder at room temperature. The term solid is defined as a physical form which does not significantly change over time, i.e., if a solid object (e.g., laundry soap bar) is placed inside a container, the solid object does not change to fill the container it is placed in. The bar is a solid typically in bar form but can be in other solid shapes such as round or oval.

The laundry soap bar may contain one or more additional enzymes, protease inhibitors such as peptide aldehydes (or hydrosulfite adduct or hemiacetal adduct), boric acid, borate, borax and/or phenylboronic acid derivatives such as 4-formylphenylboronic acid, one or more soaps or synthetic surfactants, polyols such as glycerine, pH controlling compounds such as fatty acids, citric acid, acetic acid and/or formic acid, and/or a salt of a monovalent cation and an organic anion wherein the monovalent cation may be for example $Na^+$, $K^+$ or $NH_4^+$ and the organic anion may be for example formate, acetate, citrate or lactate such that the salt of a monovalent cation and an organic anion may be, for example, sodium formate.

The laundry soap bar may also contain complexing agents like EDTA and HEDP, perfumes and/or different type of fillers, surfactants, e.g., anionic synthetic surfactants, builders, polymeric soil release agents, detergent chelators, stabilizing agents, fillers, dyes, colorants, dye transfer inhibitors, alkoxylated polycarbonates, suds suppressers, structurants, binders, leaching agents, bleaching activators, clay soil removal agents, anti-redeposition agents, polymeric dispersing agents, brighteners, fabric softeners, perfumes and/or other compounds known in the art.

The laundry soap bar may be processed in conventional laundry soap bar making equipment such as but not limited to: mixers, plodders, e.g a two stage vacuum plodder, extruders, cutters, logo-stampers, cooling tunnels and wrappers. The invention is not limited to preparing the laundry soap bars by any single method. The premix of the invention may be added to the soap at different stages of the process. For example, the premix containing soap, DNase, optionally one or more additional enzymes, a protease inhibitor, and a salt of a monovalent cation and an organic anion may be prepared and the mixture is then plodded. The DNase and optional additional enzymes may be added at the same time as the protease inhibitor for example in liquid form. Besides the mixing step and the plodding step, the process may further comprise the steps of milling, extruding, cutting, stamping, cooling and/or wrapping.

Formulation of Enzyme in Co-Granule

The DNase may be formulated as a granule for example as a co-granule that combines one or more enzymes. Each enzyme will then be present in more granules securing a more uniform distribution of enzymes in the detergent. This also reduces the physical segregation of different enzymes due to different particle sizes. Methods for producing multi-enzyme co-granulates for the detergent industry are disclosed in the IP.com disclosure IPCOM000200739D.

Another example of formulation of enzymes by the use of co-granulates are disclosed in WO 2013/188331, which relates to a detergent composition comprising (a) a multi-enzyme co-granule; (b) less than 10 wt zeolite (anhydrous basis); and (c) less than 10 wt phosphate salt (anhydrous basis), wherein said enzyme co-granule comprises from 10 to 98 wt % moisture sink component and the composition additionally comprises from 20 to 80 wt % detergent moisture sink component. WO 2013/188331 also relates to a method of treating and/or cleaning a surface, preferably a fabric surface comprising the steps of (i) contacting said surface with the detergent composition as claimed and described herein in an aqueous wash liquor, (ii) rinsing and/or drying the surface.

The multi-enzyme co-granule may comprise a DNase and (a) one or more enzymes selected from the group consisting of first-wash lipases, cleaning cellulases, xyloglucanases, perhydrolases, peroxidases, lipoxygenases, laccases and mixtures thereof; and (b) one or more enzymes selected from the group consisting of hemicellulases, proteases, care cellulases, cellobiose dehydrogenases, xylanases, phospho lipases, esterases, cutinases, pectinases, mannanases, pectate lyases, keratinases, reductases, oxidases, phenoloxidases, ligninases, pullulanases, tannases, pentosanases, lichenases glucanases, arabinosidases, hyaluronidase, chondroitinase, amylases, and mixtures thereof.

Methods and Uses of Detergent Composition

The invention further concerns a method for laundering a textile. Accordingly, one aspect of the present invention concerns a method for preventing, reducing or removing biofilm from a textile or fabric comprising:

(i) contacting the a textile or fabric with a wash liquor comprising the detergent composition according to any one of claims 1 to 15, (ii) subjecting said textile to at least one washing cycle, (iii) optionally rinsing said textile.

In a preferred embodiment, the textile is at least partly coated with a biofilm.

In one embodiment, the temperature of the wash liquor is in the range of 5° C. to 95° C., such as in the range of 10° C. to 80° C., for example in the range of 10° C. to 70° C., such as in the range of 10° C. to 60° C., for example in the range of 10° C. to 50° C., such as in the range of 15° C. to 40° C., for example in the range of 20° C. to 30° C. In one embodiment the temperature of the wash liquor is 30° C.

The pH of the liquid solution is in the range of 1 to 11, such as in the range 5.5 to 11, such as in the range of 7 to 9, in the range of 7 to 8 or in the range of 7 to 8.5. In one embodiment of the present invention, the concentration of the polypeptide having deoxyribonuclease activity in the wash liquor is within the range of 0.001 ppm to 100 ppm.

In some aspects, the invention relates to a method for preventing, reducing or removing biofilm from a textile or fabric comprising:

(i) contacting the a textile or fabric with a wash liquor with a detergent composition, comprising
  (a) a polypeptide having deoxyribonuclease activity, wherein the concentration of the DNase in the detergent is in the range of about 0.001-2 ppm enzyme protein, optionally form about 0.01-0.2 ppm enzyme protein, optionally from about 0.01-0.02 ppm enzyme protein and
  (b) at least one surfactant, wherein the total amount of surfactant(s) in said composition is in the range of 3.6 w/w % to 28.5 w/w %, optionally in the range of 3 w/w % to 30 w/w %, optionally in the range of 5 w/w % to 20 w/w %, optionally in the range of 10 w/w % to 20 w/w % or optionally in the range of 15 w/w % to 20 w/w %, optionally in the range of w/w % 10 to 15 w/w % or optionally below 20 w/w %, such as below 15 w/w % but more than 0 w/w %.

(ii) subjecting said textile to at least one washing cycle, (iii) optionally rinsing said textile.

In a preferred embodiment, the textile is at least partly coated with a biofilm.

In one embodiment, the temperature of the wash liquor is in the range of 5° C. to 95° C., such as in the range of 10° C. to 80° C., for example in the range of 10° C. to 70° C., such as in the range of 10° C. to 60° C., for example in the range of 10° C. to 50° C., such as in the range of 15° C. to 40° C., for example in the range of 20° C. to 30° C. In one embodiment the temperature of the wash liquor is 30° C.

The pH of the liquid solution is in the range of 1 to 11, such as in the range 5.5 to 11, such as in the range of 7 to 9, in the range of 7 to 8 or in the range of 7 to 8.5.

In one embodiment of the invention, the method for laundering a textile or fabric further comprises draining of the wash liquor or part of the wash liquor after completion of a wash cycle. The wash liquor can then be re-used in a subsequent wash cycle or in a subsequent rinse cycle. The textile or fabric may be exposed to the wash liquor during a first and optionally a second or a third wash cycle. In one embodiment the textile or fabric is rinsed after being exposed to the wash liquor. The textile or fabric can be rinsed with water or with water comprising a conditioner.

A further aspect of the present invention concerns the use of the detergent composition of the present invention for preventing, reducing or removing biofilm from a textile or a fabric.

Composition of Model Detergent A (Liquid)

Ingredients: 12% LAS, 11% AEO Biosoft N25-7 (NI), 7% AEOS (SLES), 6% MPG (monopropylene glycol), 3% ethanol, 3% TEA, 2.75% cocoa soap, 2.75% soya soap, 2% glycerol, 2% sodium hydroxide, 2% sodium citrate, 1% sodium formiate, 0.2% DTMPA and 0.2% PCA (all percentages are w/w).

Composition of Model Detergent B (Liquid)

Ingredients: 7.2% LAS, 6.6% AEO, 7% AEOS (SLES), 6% MPG (monopropylene glycol), 3% ethanol, 3% TEA, 2.75% cocoa soap, 2.75% soya soap, 2% glycerol, 1.2% sodium hydroxide, 2% sodium citrate, 1% sodium formiate, 0.2% DTMPA and 0.2% PCA (all percentages are w/w).

Composition of Model Detergent T (Powder)

Ingredients: 11% LAS, 2% AS, 2% soap, 3% AEO, 15.15% sodium carbonate, 3% sodium slilcate, 18.75% zeolite, 0.15% chelant, 2% sodium citrate, 1.65% AA/MA copolymer, 2.5% CMC, 44% sodium sulphate and 0.5% SRP (all percentages are w/w).

Composition of Model Detergent V (Powder)

Ingredients: 7% LAS, 1% AS, 1% soap, 3% AEO, 15% sodium carbonate, 3% sodium slilcate, 19% zeolite, 0.15% chelant, 2% sodium citrate, 1.65% AA/MA copolymer, 2.5% CMC, 44% sodium sulphate and 0.5% SRP (all percentages are w/w).

Composition of Model Detergent N (Liquid)

Ingredients: 5.3% LAS, 10.7% AEOS, 1% soap, 5.3% non-ionic surfactants, 2% sodium citrate, 0.4% TEA, 0.73 NaOH, 0.02% $CaCl_2$ add water to 100% (all percentages are w/w).

Composition of Model Detergent O (Liquid)

Ingredients: 4% LAS, 8% AEOS, 1% soap, 4% nonionic surfactants, 2% sodium citrate, 0.4% TEA, 0.60% NaOH, 0.02% $CaCl_2$, 0.1% preservatives add water to 100% (all percentages are w/w).

Composition of Model Detergent P (Liquid)

Ingredients: 2.4% LAS, 4,8% AEOS, 1% soap, 2.4% nonionic surfactants, 2% sodium citrate (trisodium citrate dehydrate), 0.4% TEA, 0.02% $CaCl_2$ (*$2H_2O$), 0.1%, pH adjusted to 8 with NaOH, add water to 100% (all percentages are w/w).

Preferred Embodiments

This section describes non-limiting embodiments of the present invention.

Paragraph 1. A detergent composition comprising:
(i) a polypeptide having deoxyribonuclease activity,
(ii) at least one surfactant,
wherein the total amount of surfactant(s) in said composition is in the range of 3.6 w/w % to 28.5 w/w %.

Paragraph 2. The detergent composition of paragraph 1, wherein said at least one sucfactant is selected from the group consisting of anionic surfactant, cationic surfactant and non-ionic surfactant.

Paragraph 3. The detergent composition of paragraph 1 or 2, wherein said total amount of surfactant(s) including soap ifoen or more soap is present in the detergent is in the range of about 2 w/w % to about about 35 w/w %, optionally in the range of about 3 w/w % to 30 w/w %, optionally in the range of about 5 w/w % to about 20 w/w %, optionally in the range of about 10 w/w % to about 20 w/w % or optionally in the range of about 15 w/w % to about 20 w/w % or optionally below 20 w/w %, such as below 15 w/w % but more than 0 w/w %.

Paragraph 4. The detergent composition of paragraph 3, wherein said composition comprises at least one anionic surfactant and the amount of said anionic surfactant(s) in said composition is in the range of 2.5 w/w % to 19.6 w/w %, optionally in the range of about 5 w/w % to about 20 w/w %, optionally in the range of about 5 w/w % to about 15 w/w % or optionally in the range of about 5 w/w % to about 10 w/w %.

Paragraph 5. The detergent compostion according to any of paragraphs 1-4, wherein said composition comprises linear alkylbenzene sulfonate (LAS).

Paragraph 6. The detergent compostion according to paragraph 5, wherein the amount of linear alkylbenzene sulfonate (LAS) in said composition is in the range of 1.2 w/w % to 9.6 w/w %, optionally in the range of about 2 w/w % to about 10 w/w %.

Paragraph 7. The detergent compostion according to any of paragraphs 1-6, wherein said composition comprises at least one alkyl ethoxysulfate (AEOS).

Paragraph 8. The detergent compostion according to paragraph 7, wherein the amount of said least one alkyl ethoxysulfate (AEOS) in said composition is in the range of 0.7 w/w % to 9.6 w/w %, optionally in the range of about 1 w/w % to about 10 w/w %.

Paragraph 9. The detergent compostion according to any of paragraphs 1-8, wherein said composition comprises at least one non-ionic surfactant and the amount of said non-ionic surfactant(s) in said composition is in the range of 1.1 w/w % to 8.8 w/w %, optionally in the range of about 2 w/w % to about 10 w/w %.

Paragraph 10. The detergent composition according to paragraph 9, wherein said least one non-ionic surfactant is AEO Biosoft N25-7.

Paragraph 11. The detergent composition according to any of paragraphs 1-10, further comprising a builder.

Paragraph 12. The detergent composition according to any of paragraphs 1-11, wherein said composition is in a solid form.

Paragraph 13. The detergent composition according to any of paragraphs 1-12, wherein said composition is in a liquid form.

Paragraph 14. The detergent composition according to paragraph 13, wherein said detergent composition comprises a solvent.

Paragraph 15. The detergent composition according to any of paragraphs 1-14, wherein the polypeptide having deoxyribonuclease activity is selected from the group consisting of a polypeptide having at least 85% sequence identity to the mature polypeptide of SEQ ID NO: 1, a polypeptide having at least 85% sequence identity to the amino acid sequence set forth in SEQ ID NO: 2, a polypeptide having at least 85% sequence identity to the amino acid sequence set fort in SEQ ID NO: 3, a polypeptide having at least 85% sequence identity to the mature polypeptide of SEQ ID NO: 4, a polypeptide having at least 85% sequence identity to the mature polypeptide of SEQ ID NO: 5 and a polypeptide having at least 85% sequence identity to the mature polypeptide of SEQ ID NO: 6.

Paragraph 16. The detergent composition according to any of paragraphs 1-15, wherein the polypeptide having deoxyribonuclease activity is selected from the group consisting of a polypeptide comprising or consisting of the mature polypeptide of SEQ ID NO: 1, a polypeptide comprising or consisting of the amino acid sequence set forth in SEQ ID NO: 2, a polypeptide comprising or consisting of the amino acid sequence set fort in SEQ ID NO: 3, a polypeptide comprising or consisting of the mature polypeptide of SEQ ID NO: 4, a polypeptide comprising or consisting of the mature polypeptide of SEQ ID NO: 5 and a polypeptide comprising or consisting of the mature polypeptide of SEQ ID NO: 6.

Paragraph 17. The detergent composition according to any of paragraphs 1-16, wherein the concentration of said polypeptide having deoxyribonuclease activity in a wash dose of said detergent composition is within the range of 0.001 ppm to 100 ppm, optionally in the range of about 0.001-2 ppm enzyme protein, optionally from about about 0.01-0.2 ppm enzyme protein or optionally from about 0.01-0.02 ppm enzyme protein.

Paragraph 18. A method for preventing, reducing or removing biofilm from a textile or fabric comprising:
(i) contacting the a textile or fabric at least partly coated with a biofilm with a wash liquor comprising the detergent composition according to any one of paragraphs 1 to 17,
(ii) subjecting said textile to at least one washing cycle,
(iii) optionally rinsing said textile.

Paragraph 19. The method according to paragraph 18, wherein the temperature of said wash liquor is in the range of 5° C. to 95° C., such as in the range of 10° C. to 80° C., for example in the range of 10° C. to 70° C., such as in the range of 10° C. to 60° C., for example in the range of 10° C. to 50° C., such as in the range of 15° C. to 40° C., for example in the range of 20° C. to 30° C.

Paragraph 20. The method according to paragraph 18 or 19, wherein the pH of the liquid solution is in the range of 1 to 11, such as in the range 5.5 to 11, such as in the range of 7 to 9, in the range of 7 to 8 or in the range of 7 to 8.5.

Paragraph 21. The method according to any of paragraphs 18-20, wherein the concentration of said polypeptide having deoxyribonuclease activity in the wash liquor is within the range of 0.001 ppm to 100 ppm, optionally in the range of about 0.001-2 ppm enzyme protein, optionally from about about 0.01-0.2 ppm enzyme protein, optionally from about about 0.2-0.5 ppm enzyme protein or optionally from about 0.01-0.02 ppm enzyme protein.

Paragraph 22. Use of the detergent composition according to any of paragraphs 1-17 for preventing, reducing or removing biofilm from a textile or a fabric.

Wash Assays

Mini Launder-O-Meter (MiniLOM) Model Wash System

MiniLOM is a modified mini wash system of the Launder-O-Meter (LOM), which is a medium scale model wash system that can be applied to test up to 20 different wash conditions simultaneously. A LOM is basically a large temperature controlled water bath with 20 closed metal beakers rotating inside it. Each beaker constitutes one small washing machine and during an experiment, each will contain a solution of a specific detergent/enzyme system to be tested along with the soiled and unsoiled fabrics it is tested on. Mechanical stress is achieved by the beakers being rotated in the water bath and by including metal balls in the beaker.

The LOM model wash system is mainly used in medium scale testing of detergents and enzymes at European wash conditions. In a LOM experiment, factors such as the ballast to soil ratio and the fabric to wash liquor ratio can be varied. Therefore, the LOM provides the link between small scale experiments, such as AMSA and mini-wash, and the more time consuming full scale experiments in front loader washing machines.

In miniLOM, washes are performed in 50 ml test tubes placed in Stuart rotator.

Terg-O-Timeter (TOM) Wash Aassay

The Tergo-To-Meter (TOM) is a medium scale model wash system that can be applied to test 12 different wash conditions simultaneously. A TOM is basically a large temperature controlled water bath with up to 12 open metal beakers submerged into it. Each beaker constitutes one small top loader style washing machine and during an experiment, each of them will contain a solution of a specific detergent/enzyme system and the soiled and unsoiled fabrics its performance is tested on. Mechanical stress is achieved by a rotating stirring arm, which stirs the liquid within each beaker. Because the TOM beakers have no lid, it is possible to withdraw samples during a TOM experiment and assay for information on-line during wash.

The TOM model wash system is mainly used in medium scale testing of detergents and enzymes at US or LA/AP wash conditions. In a TOM experiment, factors such as the ballast to soil ratio and the fabric to wash liquor ratio can be varied. Therefore, the TOM provides the link between small scale experiments, such as AMSA and mini-wash, and the more time consuming full scale experiments in top loader washing machines.

Equipment: The water bath with 12 steel beakers and 1 rotating arm per beaker with capacity of 500 or 1200 mL of detergent solution. Temperature ranges from 5 to 80° C. The water bath has to be filled up with deionised water. Rotational speed can be set up to 70 to 120 rpm/min.

Set temperature in the Terg-O-Tometer and start the rotation in the water bath. Wait for the temperature to adjust (tolerance is +/−0.5° C.). All beakers shall be clean and without traces of prior test material.

The wash solution with desired amount of detergent, temperature and water hardness is prepared in a bucket. The detergent is allowed to dissolve during magnet stirring for 10 min. Wash solution shall be used within 30 to 60 min after preparation.

800 ml wash solution is added into a TOM beaker. The wash solution is agitated at 120 rpm and optionally one or more enzymes are added to the beaker. The swatches are sprinkled into the beaker and then the ballast load. Time measurement starts when the swatches and ballast are added to the beaker. The swatches are washed for 20 minutes after which agitation is terminated. The wash load is subsequently transferred from the TOM beaker to a sieve and rinse with cold tap water. The soid swatches are separated from the ballast load. The soil swatches are transferred to a 5 L beaker with cold tap water under running water for 5 minutes. The ballast load is kept separately for the coming inactivation. The water is gently pressed out of the swatches by hand and placed on a tray covered with a paper. Another paper is placed on top of the swatches. The swatches are allowed to dry overnight before subjecting the swatches to analysis, such as measuring the color intensity using a Color Eye as described herein.

EXAMPLES

Example 1

Materials and Methods
Isolating Laundry Specific Bacterial Strains

One strain of *Brevundimonas* sp. isolated from laundry was used in the present example. The *Brevundimonas* sp. was isolated during a study, where the bacterial diversity in laundry after washing at 15, 40 and 60° C., respectively, was investigated. The study was conducted on laundry collected from Danish households. For each wash, 20 g of laundry items (tea towel, towel, dish cloth, bib, T-shirt armpit, T-shirt collar, socks) in the range 4:3:2:2:1:1:1 was used. Washing was performed in a Laundr-O-Meter (LOM) at 15, 40 or 60° C. For washing at 15 and 40° C., Ariel Sensitive White & Color was used, whereas WFK I EC-A* model detergent was used for washing at 60° C. Ariel Sensitive White & Color was prepared by weighing out 5.1 g and adding tap water up to 1000 ml followed by stirring for 5 minutes. WFK I EC-A* model detergent (which is available from WFK Testgewebe GmbH) was prepared by weighing out 5 g and adding tap water up to 1300 ml followed by stirring for 15 min. Washing was performed for 1 hour at 15, 40 and 60° C., respectively, followed by 2 times rinsing with tap water for 20 min at 15° C.

Laundry was sampled immediately after washing at 15, 40 and 60° C., respectively. Twenty grams of laundry was added 0.9% (w/v) NaCl (1.06404; Merck, Damstadt, Germany) with 0.5% (w/w) tween 80 to yield a 1:10 dilution in stomacher bag. The mixture was homogenized using a Stomacher for 2 minutes at medium speed. After homogenization, ten-fold dilutions were prepared in 0.9% (w/v) NaCl. Bacteria were enumerated on Tryptone Soya Agar (TSA) (CM0129, Oxoid, Basingstoke, Hampshire, UK) incubated aerobically at 30° C. for 5-7 days. To suppress growth of yeast and moulds, 0.2% sorbic acid (359769, Sigma) and 0.1% cycloheximide (18079; Sigma) were added. Bacterial colonies were selected from countable plates and purified by restreaking twice on TSA. For long time storage, purified isolates were stored at −80° C. in TSB containing 20% (w/v) glycerol (49779; Sigma).

Preparation of Biofilm Swatches

In the present study, one strain of *Brevundimonas* sp. was used. *Brevundimonas* sp. was pre-grown on Tryptone Soya Agar (TSA) (pH 7.3) (CM0131; Oxoid Ltd, Basingstoke, UK) for 2-5 days at 30° C. From a single colony, a loop-full was transferred to 10 mL of TSB (Tryptone Soya broth, Oxoid) and incubated for 1 day at 30° C. with shaking (240 rpm). After propagation, *Brevundimonas* sp. was pelleted by centrifugation (Sigma Laboratory Centrifuge 6K15) (3000 g at 21° C. in 7 min) and resuspended in 10 mL of TSB diluted twice with water. Optical density (OD) at 600 nm was measured using a spectophometer (POLARstar Omega (BMG Labtech, Ortenberg, Germany). Fresh TSB diluted twice with water was inoculated to an OD600 nm of 0.03, and 20 mL was added into a petridish (diameter 8.5 cm), in which a swatch of polyester (WFK 30A) measuring 5 cm×5 cm were placed. After incubation (24 h at 15° C. with shaking (100 rpm), swatches were rinsed twice with 0.9% (w/v) NaCl.

Washing Experiment

Model detergent A wash liquor (100%) was prepared by dissolving 3.33 g/l of model detergent A containing 12% LAS, 11% AEO Biosoft N25-7 (NI), 7% AEOS (SLES), 6% MPG, 3% ethanol, 3% TEA (triethanolamine), 2.75% cocoa soap, 2.75% soya soap, 2% glycerol, 2% sodium hydroxide, 2% sodium citrate, 1% sodium formiate, 0.2% DTMPA and 0.2% PCA (all percentages are w/w) in water with hardness 15° dH. Wash liquors containing 80, 60, 40, 20 and 10% of model detergent A were prepared by diluting model detergent A wash liquor (100%) in water with hardness 15° dH. TOM beakers were added model detergent A wash liquor (1000 ml) and then pigment soil (Pigmentschmutz, 09V, wfk, Krefeld, Germany) (0.7 g/L). In washes with DNase, *Aspergillus oryzae* DNase (0.5 ppm) were added to the wash liquor. Five rinsed swatches with *Brevundimonas* sp. and mixed textile giving a total weight of 10 g were added to the TOM beakers and washing were carried out for 30 min at 30° C. at 110 rpm. After washing, swatches with *Brevundimonas* sp. were rinsed twice in tap water and dried on filter paper over night. Color difference (L values) was measured using a Color Eye (Macbeth Color Eye 7000 reflectance spectrophotometer). The measurements were made without UV in the incident light and the L value from the CIE Lab color space was extracted.

TABLE 1

| Dose of detergent (%) | Type of textile | L-value$_{with\ DNase}$ | L-value$_{without\ DNase}$ | $\dfrac{\text{L-value}_{with\ DNase}}{\text{L-value}_{without\ DNase}}$ |
|---|---|---|---|---|
| 100 | Polyester | 87.6 | 85.8 | 1.7 |
| 80 | Polyester | 87.5 | 86.0 | 1.5 |
| 60 | Polyester | 87.4 | 85.3 | 2.1 |
| 40 | Polyester | 86.0 | 84.1 | 1.9 |
| 20 | Polyester | 86.5 | 85.3 | 1.2 |
| 10 | Polyester | 85.6 | 83.2 | 2.4 |

Example 2

Preparation of Swatches with Biofilm

*Brevundimonas* sp. (isolated as described in Example 1) was pre-grown on Tryptone Soya Agar (TSA) (pH 7.3) (CM0131; Oxoid Ltd, Basingstoke, UK) for 2-5 days at 30° C. From a single colony, a loop-full was transferred to 10 mL of TSB and incubated for 1 day at 30° C. with shaking (240 rpm). After propagation, *Brevundimonas* sp. was pelleted by centrifugation (Sigma Laboratory Centrifuge 6K15) (3000 g at 21° C. in 7 min) and resuspended in 10 mL of TSB diluted twice with water. Optical density (OD) at 600 nm was measured using a spectophometer (POLARstar Omega (BMG Labtech, Ortenberg, Germany). Fresh TSB diluted twice with water was inoculated to an OD$_{600nm}$ of 0.03, and 1.6 mL was added into each well of a 12-well polystyrene flat-bottom microplate (3512; Corning Incorporated, Corning, N.Y., USA), in which a round swatch (diameter 2 cm) of sterile Polyester WFK30A was placed. After incubation (24 h at 15° C. with shaking (100 rpm), swatches were rinsed twice with 0.9% (w/v) NaCl.

Wash Experiment

Wash liquors of liquid model detergent A, liquid model detergent B, powder model detergent T, powder model detergent V, liquid model detergent N, liquid model detergent O and liquid model detergent P were prepared by weighing out and dissolving detergents in water with water with hardness 15° dH. Dosing of model detergent A and B was 3.33 g/L, whereas dosing of model detergent T and V was 5.30 g/L. The AEO Biosoft N25-7 (NI) (0.16 g/l) component of model detergent T and V was added separately. Dosing of model detergent O, P and V was 5.30 g/L and water hardness was 15° dH. Pigment soil (Pigmentschmutz, 09V, wfk, Krefeld, Germany) (0.7 g/L) was added to the wash liquors, and 10 ml was added to a 50 ml test tube in which five rinsed swatches with *Brevundimonas* sp. biofilm and five sterile polyester (WFK30A) swatches were placed. In washes, where *A. oryzae* DNase (mature polypeptide of SEQ ID NO: 1) was included, DNase (0.5 ppm) was added to wash liquors. In washes, where *T. harzianum* DNase (mature polypeptide of SEQ ID NO: 4) was included, DNase (0.5 ppm) was added to wash liquors. In washes, where *B. licheniformis* DNase (mature polypeptide of SEQ ID NO: 5) was included, DNase (0.5 ppm) was added to wash liquors. In washes, where *B. subtilis* DNase (mature polypeptide of SEQ ID NO: 6) was included, DNase (0.5 ppm) was added to wash liquors. Test tubes were placed in a Stuart rotator (Mini LOM) for 1 hour at 30° C. Swatches were rinsed twice with tap water and dried on filter paper over night. Color difference (L values) was measured using a Color Eye (Macbeth Color Eye 7000 reflectance spectrophotometer). The measurements were made without UV in the incident light and the L value from the CIE Lab color space was extracted. The color difference (L value, L*) represents the darkest black at L*=0, and the brightest white at L*=100. Data is represented as Delta L values meaning the L value of the swatch washed with DNase minus the L value of swatch washed without DNase.

TABLE 2

Deep cleaning by *A. oryzae* DNase in liquid and powder detergents with reduced level of surfactants.

| Detergent | Forhmat | Surfactant Level | DNase | $L_{Biofilm\ swatches}$ | $\Delta L_{Biofilm\ swatches}$ $(L_{(DNase)} - L_{(no\ DNase)})$ | $L_{Sterile\ swatches}$ | $\Delta L_{Sterile\ swatches}$ $(L_{(DNase)} - L_{(no\ DNase)})$ |
|---|---|---|---|---|---|---|---|
| Model detergent A | Liquid | Normal | + | 87.5 | 6.6 | 87.7 | 4.0 |
| Model detergent A | Liquid | Normal | − | 80.9 | | 83.7 | |
| Model detergent B | Liquid | Low | + | 88.4 | 6.1 | 88.9 | 4.0 |
| Model detergent B | Liquid | Low | − | 82.3 | | 84.9 | |
| Model detergent T | Powder | Normal | + | 88.9 | 5.2 | 86.2 | 4.4 |
| Model detergent T | Powder | Normal | − | 83.7 | | 81.8 | |
| Model detergent V | Powder | Low | + | 88.5 | 4.3 | 87.7 | 2.4 |
| Model detergent V | Powder | Low | − | 84.2 | | 85.3 | |

For clarity the surfactant level of the table above could be explained as if normal=100 and low=60, then the surfactant level is reduced by 40%.

TABLE 3

In table 3 Results of washes with detergents comprising different level of surfactants, where *A. oryzae* ($L_{(DNaseAo)}$), *T. harzianum* ($L_{(DNaseTh)}$), *B. licheniformis* ($L_{(DNaseBl)}$) and *B. subtilis* ($L_{(DNaseBs)}$) DNase (0.5 ppm) was added to wash liquors or not added.

| Detergent | Format | Surfactant level with soap | Surfactant level without soap | DNase | $L_{Biofilm\ swatches}$ | $\Delta L_{Biofilm\ swatches}$ $(L_{(DNaseAo)} - L_{(no\ DNase)})$ | $L_{Sterile\ swatches}$ | $\Delta L_{Sterile\ swatches}$ $(L_{(DNaseAo)} - L_{(no\ DNase)})$ |
|---|---|---|---|---|---|---|---|---|
| Model detergent A | Liquid | 33.5 | 28.0 | + | 88.2 | 4.6 | 88.2 | 0.9 |
| Model detergent A | Liquid | 33.5 | 28.0 | − | 83.7 | | 87.3 | |
| Model detergent B | Liquid | 22.1 | 16.6 | + | 88.8 | 3.8 | 89.3 | 0.6 |
| Model detergent B | Liquid | 22.1 | 16.6 | − | 85.0 | | 88.7 | |
| Model detergent T | Powder | 17.0 | 15.0 | + | 89.6 | 5.2 | 87.3 | 0.6 |

TABLE 3-continued

In table 3 Results of washes with detergents comprising different level of surfactants, where *A. oryzae* ($L_{DNaseAo}$), *T. harzianum* ($L_{DNaseTh}$), *B. licheniformis* ($L_{DNaseBl}$) and *B. subtilis* ($L_{DNaseBs}$) DNase (0.5 ppm) was added to wash liquors or not added.

| Detergent | Format | Surfactant level with soap | Surfactant level without soap | DNase | $L_{Biofilm\ swatches}$ | $\Delta L_{Biofilm\ swatches}$ | $L_{Sterile\ swatches}$ | $\Delta L_{Sterile\ swatches}$ |
|---|---|---|---|---|---|---|---|---|
| Model detergent T | Powder | 17.0 | 15.0 | − | 84.4 | | 86.7 | |
| Model detergent V | Powder | 10.2 | 9.0 | + | 88.1 | 4.0 | 88.8 | 3.0 |
| Model detergent V | Powder | 10.2 | 9.0 | − | 84.1 | | 85.8 | |
| Model detergent N | Liquid | 22.3 | 21.3 | + | 85.3 | 4.6 | 85.1 | 2.7 |
| Model detergent N | Liquid | 22.3 | 21.3 | − | 80.7 | | 82.4 | |
| Model detergent O | Liquid | 17.0 | 16.0 | + | 85.0 | 3.0 | 85.7 | 1.6 |
| Model detergent O | Liquid | 17.0 | 16.0 | − | 82.0 | | 84.2 | |
| Model detergent P | Liquid | 10.6 | 9.6 | + | 87.2 | 4.3 | 87.1 | 2.6 |
| Model detergent P | Liquid | 10.6 | 9.6 | − | 82.9 | | 84.5 | |

| Detergent | Format | Surfactant level with soap | Surfactant level without soap | DNase | $L_{Biofilm\ swatches}$ | $\Delta L_{Biofilm\ swatches}$ ($L_{(DNaseTh)} - L_{(no\ DNase)}$) | $L_{Sterile\ swatches}$ | $\Delta L_{Sterile\ swatches}$ ($L_{(DNaseTh)} - L_{(no\ DNase)}$) |
|---|---|---|---|---|---|---|---|---|
| Model detergent A | Liquid | 33.5 | 28.0 | + | 86.5 | 2.9 | 88.2 | 0.9 |
| Model detergent A | Liquid | 33.5 | 28.0 | − | 83.7 | | 87.3 | |
| Model detergent B | Liquid | 22.1 | 16.6 | + | 89.1 | 4.1 | 90.2 | 1.6 |
| Model detergent B | Liquid | 22.1 | 16.6 | − | 85.0 | | 88.7 | |
| Model detergent T | Powder | 17.0 | 15.0 | + | 87.0 | 2.6 | 87.0 | 0.3 |
| Model detergent T | Powder | 17.0 | 15.0 | − | 84.4 | | 86.7 | |
| Model detergent V | Powder | 10.2 | 9.0 | + | 87.2 | 3.1 | 87.9 | 2.1 |
| Model detergent V | Powder | 10.2 | 9.0 | − | 84.1 | | 85.8 | |
| Model detergent N | Liquid | 22.3 | 21.3 | + | 84.8 | 4.0 | 84.9 | 2.5 |
| Model detergent N | Liquid | 22.3 | 21.3 | − | 80.7 | | 82.4 | |
| Model detergent O | Liquid | 17.0 | 16.0 | + | 85.1 | 3.1 | 86.3 | 2.1 |
| Model detergent O | Liquid | 17.0 | 16.0 | − | 82.0 | | 84.2 | |
| Model detergent P | Liquid | 10.6 | 9.6 | + | 86.8 | 3.9 | 87.0 | 2.5 |
| Model detergent P | Liquid | 10.6 | 9.6 | − | 82.9 | | 84.5 | |

TABLE 3-continued

In table 3 Results of washes with detergents comprising different level of surfactants, where
A. oryzae (L$_{(DNaseAo)}$), T. harzianum (L$_{(DNaseTh)}$), B. licheniformis (L$_{(DNaseBl)}$) and B. subtilis
(L$_{(DNaseBs)}$) DNase (0.5 ppm) was added to wash liquors or not added.

| Detergent | Format | Surfactant level with soap | Surfactant level without soap | DNase | L$_{Biofilm\ swatches}$ | ΔL$_{Biofilm\ swatches}$ (L$_{(DNaseBl)}$ − L$_{(no\ DNase)}$) | L$_{Sterile\ swatches}$ | ΔL$_{Sterile\ swatches}$ (L$_{(DNaseBl)}$ − L$_{(no\ DNase)}$) |
|---|---|---|---|---|---|---|---|---|
| Model detergent A | Liquid | 33.5 | 28.0 | + | 87.9 | 4.3 | 87.8 | 0.5 |
| Model detergent A | Liquid | 33.5 | 28.0 | − | 83.7 | | 87.3 | |
| Model detergent B | Liquid | 22.1 | 16.6 | + | 88.1 | 3.1 | 88.8 | 0.1 |
| Model detergent B | Liquid | 22.1 | 16.6 | − | 85.0 | | 88.7 | |
| Model detergent T | Powder | 17.0 | 15.0 | + | 88.2 | 3.8 | 87.0 | 0.3 |
| Model detergent T | Powder | 17.0 | 15.0 | − | 84.4 | | 86.7 | |
| Model detergent V | Powder | 10.2 | 9.0 | + | 88.5 | 4.4 | 86.5 | 0.7 |
| Model detergent V | Powder | 10.2 | 9.0 | − | 84.1 | | 85.8 | |
| Model detergent N | Liquid | 22.3 | 21.3 | + | 84.9 | 4.2 | 85.5 | 3.1 |
| Model detergent N | Liquid | 22.3 | 21.3 | − | 80.7 | | 82.4 | |
| Model detergent O | Liquid | 17.0 | 16.0 | + | 85.1 | 3.1 | 85.9 | 1.7 |
| Model detergent O | Liquid | 17.0 | 16.0 | − | 82.0 | | 84.2 | |
| Model detergent P | Liquid | 10.6 | 9.6 | + | 86.9 | 4.1 | 87.1 | 2.6 |
| Model detergent P | Liquid | 10.6 | 9.6 | − | 82.9 | | 84.5 | |

| Detergent | Format | Surfactant level with soap | Surfactant level without soap | DNase | L$_{Biofilm\ swatches}$ | ΔL$_{Biofilm\ swatches}$ (L$_{(DNaseBs)}$ − L$_{(no\ DNase)}$) | L$_{Sterile\ swatches}$ | ΔL$_{Sterile\ swatches}$ (L$_{(DNaseBs)}$ − L$_{(no\ DNase)}$) |
|---|---|---|---|---|---|---|---|---|
| Model detergent A | Liquid | 33.5 | 28.0 | + | 87.5 | 3.8 | 87.6 | 0.3 |
| Model detergent A | Liquid | 33.5 | 28.0 | − | 83.7 | | 87.3 | |
| Model detergent B | Liquid | 22.1 | 16.6 | + | 89.4 | 4.4 | 89.4 | 0.8 |
| Model detergent B | Liquid | 22.1 | 16.6 | − | 85.0 | | 88.7 | |
| Model detergent T | Powder | 17.0 | 15.0 | + | 88.0 | 3.6 | 87.3 | 0.5 |
| Model detergent T | Powder | 17.0 | 15.0 | − | 84.4 | | 86.7 | |
| Model detergent V | Powder | 10.2 | 9.0 | + | 86.6 | 2.4 | 85.3 | −0.5 |

TABLE 3-continued

In table 3 Results of washes with detergents comprising different level of surfactants, where
*A. oryzae* (L$_{(DNaseAo)}$), *T. harzianum* (L$_{(DNaseTh)}$), *B. licheniformis* (L$_{(DNaseBl)}$) and *B. subtilis*
(L$_{(DNaseBs)}$) DNase (0.5 ppm) was added to wash liquors or not added.

| | | | | | | | | |
|---|---|---|---|---|---|---|---|---|
| Model detergent V | Powder | 10.2 | 9.0 | − | 84.1 | | 85.8 | |
| Model detergent N | Liquid | 22.3 | 21.3 | + | 83.0 | 2.3 | 84.8 | 2.4 |
| Model detergent N | Liquid | 22.3 | 21.3 | − | 80.7 | | 82.4 | |
| Model detergent O | Liquid | 17.0 | 16.0 | + | 86.4 | 4.3 | 86.7 | 2.6 |
| Model detergent O | Liquid | 17.0 | 16.0 | − | 82.0 | | 84.2 | |
| Model detergent P | Liquid | 10.6 | 9.6 | + | 86.5 | 3.6 | 86.6 | 2.0 |
| Model detergent P | Liquid | 10.6 | 9.6 | − | 82.9 | | 84.5 | |

Firstly, table 3 shows that all the tested DNases have effect on biofilm swatch tested and that the effect is maintained when the amount of surfactant is reduced, e.g., performance of the DNases in detergents with surfactant level (total amount of surfactant with soap) about 30, e.g., 33.5 (Model A) is compared to performance of the DNases in detergents with surfactant level (total amount of surfactant with soap) about 17 (Model T). A specific example the DNase from *Bacillus subtilis* (DNaseBs) mature polypeptide of SEQ ID NO: 6 have comparable performance in Model detergent O (total amount of surfactant with soap 17) and Model P (total amount of surfactant with soap about 11 (10.6). In other words the surfactant level does not influence the performance of the DNases and the effect of the DNases is maintained even in detergents with surfactant levels (total amount with soap) of about 11.

The invention claimed is:

1. A detergent composition comprising:
   (a) a polypeptide having deoxyribonuclease activity, wherein the polypeptide has at least 85% sequence identity to a polypeptide selected from the group consisting of SEQ ID NO: 1, SEQ ID NO: 2, and SEQ ID NO: 3; and
   (b) at least one surfactant,
   wherein the total amount of surfactant(s) in said composition is in the range of 3.6 w/w % to 28.5 w/w %.

2. The detergent composition of claim 1, wherein the at least one surfactant is selected from the group consisting of anionic surfactants, cationic surfactants and non-ionic surfactants.

3. The detergent composition of claim 2, wherein the composition comprises at least one anionic surfactant and the amount of said anionic surfactant(s) in said composition is in the range of 2.5 w/w % to 19.6 w/w %.

4. The detergent composition of claim 1, wherein the at least one surfactant comprises linear alkylbenzene sulfonate (LAS).

5. The detergent composition of claim 4, wherein the amount of linear alkylbenzene sulfonate (LAS) in said composition is in the range of 1.2 w/w % to 9.6 w/w %.

6. The detergent composition of claim 1, wherein the at least one surfactant comprises at least one alkyl ethoxysulfate (AEOS).

7. The detergent composition of claim 6, wherein the amount of said at least one alkyl ethoxysulfate (AEOS) in the composition is in the range of 0.7 w/w % to 5.6 w/w %.

8. The detergent composition of claim 1, wherein the at least one surfactant comprises at least one non-ionic surfactant and the amount of the non-ionic surfactant(s) in the composition is in the range of 1.1 w/w % to 8.8 w/w %.

9. The detergent composition of claim 8, wherein the at least one non-ionic surfactant is AEO Biosoft N25-7.

10. The detergent composition of claim 1, further comprising a builder.

11. The detergent composition of claim 1, wherein the composition is in a solid form.

12. The detergent composition of claim 1, wherein the composition is in a liquid form.

13. The detergent composition of claim 4, wherein the detergent composition comprises a solvent.

14. The detergent composition of claim 1, wherein the polypeptide having deoxyribonuclease activity is selected from the group consisting of
    a polypeptide having at least 90% sequence identity to the mature polypeptide of SEQ ID NO: 1,
    a polypeptide having at least 90% sequence identity to the amino acid sequence set forth in SEQ ID NO: 2, and
    a polypeptide having at least 90% sequence identity to the amino acid sequence set forth in SEQ ID NO: 3.

15. The detergent composition of claim 1, wherein the polypeptide having deoxyribonuclease activity is selected from the group consisting of
    a polypeptide comprising or consisting of the mature polypeptide of SEQ ID NO: 1,
    a polypeptide comprising or consisting of the amino acid sequence set forth in SEQ ID NO: 2, and
    a polypeptide comprising or consisting of the amino acid sequence set forth in SEQ ID NO: 3.

16. The detergent composition of claim 1, wherein the concentration of the polypeptide having deoxyribonuclease activity in a wash dose of the detergent composition is within the range of 0.001 ppm to 100 ppm.

17. The detergent composition of claim 1, wherein the total amount of surfactant(s) including soap in the composition is in the range of about 5 w/w % to about 20 w/w %.

* * * * *